US012590295B2

(12) United States Patent
Chan et al.

(10) Patent No.: US 12,590,295 B2
(45) Date of Patent: Mar. 31, 2026

(54) MESENCHYMAL STROMAL CELLS AS A REPROGRAMMING SOURCE FOR iPSC INDUCTION

(71) Applicant: THE UNIVERSITY OF HONG KONG, Hong Kong (CN)

(72) Inventors: Chi-Fung Chan, Hong Kong (CN); Kenneth Richard Boheler, Odenton, MD (US); Jiangang Shen, Hong Kong (CN); Ruixia Deng, Hong Kong (CN); Hing Yee Law, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 640 days.

(21) Appl. No.: 17/756,711

(22) PCT Filed: Nov. 27, 2020

(86) PCT No.: PCT/CN2020/132241
§ 371 (c)(1),
(2) Date: May 31, 2022

(87) PCT Pub. No.: WO2021/104453
PCT Pub. Date: Jun. 3, 2021

(65) Prior Publication Data
US 2023/0167412 A1 Jun. 1, 2023

Related U.S. Application Data

(60) Provisional application No. 62/941,843, filed on Nov. 28, 2019.

(51) Int. Cl.
*A61P 37/02* (2006.01)
*C12N 5/0775* (2010.01)

(52) U.S. Cl.
CPC ............ *C12N 5/0668* (2013.01); *A61P 37/02* (2018.01); *C12N 2500/25* (2013.01); *C12N 2501/11* (2013.01); *C12N 2501/115* (2013.01); *C12N 2501/15* (2013.01); *C12N 2501/20* (2013.01)

(58) Field of Classification Search
CPC .............. C12N 5/0668; C12N 2501/11; C12N 2501/115; A61K 35/28
See application file for complete search history.

(56) References Cited

U.S. PATENT DOCUMENTS

2018/0055887 A1 3/2018 Lu et al.

FOREIGN PATENT DOCUMENTS

| WO | 2011/091475 A1 | 8/2011 |
| WO | 2013/082509 A1 | 6/2013 |
| WO | 2014/011881 A2 | 1/2014 |
| WO | 2014/146057 A2 | 9/2014 |
| WO | 2017/156580 A1 | 9/2017 |
| WO | 2019/111198 A1 | 6/2019 |

OTHER PUBLICATIONS

Göbel, C., Goetzke, R., Eggermann, T. et al. Interrupted reprogramming into induced pluripotent stem cells does not rejuvenate human mesenchymal stromal cells. Sci Rep 8, 11676 (2018). https://doi.org/10.1038/s41598-018-30069-6 (Year: 2018).*

Jiang B, Yan L, Wang X, Li E, Murphy K, Vaccaro K, Li Y, Xu RH. Concise Review: Mesenchymal Stem Cells Derived from Human Pluripotent Cells, an Unlimited and Quality-Controllable Source for Therapeutic Applications. Stem Cells. May 2019;37(5):572-581. doi: 10.1002/stem.2964. (Year: 2019).*

Jeong J, Shin K, Lee SB, Lee DR, Kwon H. Patient-tailored application for Duchene muscular dystrophy on mdx mice based induced mesenchymal stem cells. Exp Mol Pathol. Oct. 2014;97(2):253-8. doi: 10.1016/j.yexmp.2014.08.001. Epub Aug. 4, 2014. PMID: 25102299. (Year: 2014).*

Chen YS, Pelekanos RA, Ellis RL, Horne R, Wolvetang EJ, Fisk NM. Small molecule mesengenic induction of human induced pluripotent stem cells to generate mesenchymal stem/stromal cells. Stem Cells Transl Med. Feb. 2012;1(2):83-95. doi: 10.5966/sctm.2011-0022. Epub Feb. 7, 2012. (Year: 2012).*

Tsai TL, Manner PA, Li WJ. Regulation of mesenchymal stem cell chondrogenesis by glucose through protein kinase C/transforming growth factor signaling. Osteoarthritis Cartilage. Feb. 2013;21(2):368-76. doi: 10.1016/j.joca.2012.11.001. Epub Nov. 11, 2012. PMID: 23151458. (Year: 2012).*

International Search Report dated Feb. 25, 2021, in International Application No. PCT/CN2020/132241.

Hu, S., et al., "Effects of cellular origin on differentiation of human induced pluripotent stem cell-derived endothelial cells," JCI Insight, 2016, 1(8):1-12.

Kyttala, A., et al., "Genetic Variability Overrides the Impact of Parental Cell Type and Determines iPSC Differentiation Potential," Stem Cell Reports, 2016, 6:200-212.

Sell, S., "Stem Cells Handbook," 2013, Springer Science & Buisiness Media, pp. 1-524.

Becker, A.J., et al., "Cytological Demonstration of the Clonal Nature of Spleen Colonies Derived from Transplanted Mouse Marrow Cells," Nature, 1963, 197(4866):452-454.

Dominici, M., et al., "Minimal criteria for defining multipotent mesenchymal stromal cells. The International Society for Cellular Therapy position statement," Cytotherapy, 2006, 8(4):315-317.

Deng, R., et al., "Mini Review: Application of Human Mesenchymal Stem Cells in Gene and Stem Cells Therapy Era," Current Stem Cell Reports, 2018, 4:327-337.

Ankrum, J.A., et al., "Mesenchymal stem cells: immune evasive, not immune privileged," Nature Biotechnology, 2014, 32(3):252-260.

Kyurkchiev, D., et al., "Secretion of immunoregulatory cytokines by mesenchymal stem cells," World J Stem Cells, 2014, 6(5):1-35.

(Continued)

*Primary Examiner* — Fereydoun G Sajjadi
*Assistant Examiner* — Qinhua Gu
(74) *Attorney, Agent, or Firm* — SALIWANCHIK, LLOYD & EISENSCHENK

(57) ABSTRACT

Provided are mesenchymal stromal cells as a reprogramming source for ipsc induction. In particular, Provided is a method for generating induced mesenchymal stromal cells (iMSCs), the iMSC generated by the method as well as the use thereof.

1 Claim, 19 Drawing Sheets

(56) References Cited

OTHER PUBLICATIONS

Galipeau, J., et al., "Mesenchymal Stromal Cells: Clinical Challenges and Therapeutic Opportunities," Cell Stem Cell, 2018, 22:824-833.

Bai, L., et al., "Hepatocyte growth factor mediates mesenchymal stem cell-induced recovery in multiple sclerosis models," Nature Neuroscience, 2012, 15(6):1-10.

Mihara, K., et al., "Development and functional characterization of human bone marrow mesenchymal cells immortalized by enforced expression of telomerase," British Journal of Haematology, 2003, 120:846-849.

Lian, Q., et al., "Functional Mesenchymal Stem Cells Derived From Human Induced Pluripotent Stem Cells Attenuate Limb Ischemia in Mice," Circulation, 2010, 121:1113-1123.

Takahashi, K., et al., "Induction of Pluripotent Stem Cells from Adult Human Fibroblasts by Defined Factors," Cell, 2007, 131:861-872.

Malik, N., et al., "A Review of the Methods for Human iPSC Derivation," Methods Mol Biol, 2013, 997:23-33.

Warren, L., "Highly Efficient Reprogramming to Pluripotency and Directed Differentiation of Human Cells with Synthetic Modified mRNA," Cell Stem Cell, 2010, 7:618-630.

Subramanyam, D., et al., "Multiple targets of miR-302 and MiR-372 promote reprogramming of human fibroblasts to induced pluripotent stem cells," Nature Biotechnology, 2011, 29(5):443-449.

Anokye-Danso, F., et al., "Highly Efficient miRNA-Mediated Reprogramming of Mouse and Human Somatic Cells to Pluripotency," Cell Stem Cell, 2011, 8:1-15.

Miyoshi, N., et al., "Reprogramming of Mouse and Human Cells to Pluripotency Using Mature MicroRNA's," Cell Stem Cell, 2011, 8:633-638.

Okita, K., et al., "Generation of Mouse Induced Pluripotent Stem Cells Without Viral Vectors," Science, 2008, pp. 1-7.

Loh, Y.-H., et al., "Reprogramming of T Cells from Human Peripheral Blood," Cell Stem Cell, 2010, 7:15-19.

Staerk, J., et al., "Reprogramming of Human Peripheral Blood Cells to Induced Pluripotent Stem Cells," Cell Stem Cell, 2010, 7:20-24.

Megges, M., et al., "Generation of an iPS cell line from bone marrow derived mesenchymal stromal cells from an elderly patient," Stem Cell Research, 2015, 15:565-568.

Re, S., et al., "Imrpoved Generation of Induced Pluripotent Stem Cells From Hair Derived Keratinocytes—A Tool to Study Neurodevelopmental Disorders as ADHD," Frontiers in Cellular Neuroscience, 2018, 12(321):1-11.

Boonkaew, B., et al., "Establishment of an integration-free induced pluripotent stem cell line (MUSIi005-A) from exfoliated renal epithelial cells," Stem Cell Research, 2018, 30:34-37.

Zhang, S.-Z., et al., "Urine-derived induced pluripotent stem cells as a modeling tool for paroxysmal kinesigenic dyskinea," Biology Open, 2015, 4:1744-1752.

Zhou, T., et al., "Generation of human induced pluripotent stem cells from urine samples," Nature Protocols, 2012, 7(12):2080-2089.

Bilousova, G., et al., "Osteoblasts Derived from Induced Pluripotent Stem Cells form Calcified Structures in Scaffolds Both in Vitro and In Vivo," Stem Cells, 2011, 29:1-12.

Villa-Diaz, L.G., et al., "Derivation of Mesenchymal Stem Cells from Human Induced Pluripotent Stem Cells Cultured on Synthetic Substrates," Stem Cells, 2012, 30:1-9.

Kagia, A., et al., "Therapeutic Effects of Mesenchymal Stem Cells Derived From Bone Marrow, Umbilical Cord Blood, and Pluripotent Stem Cells in a Mouse Model of Chemically Induced Inflammatory Bowel Disease," Inflammation, 2019, 42(5):1730-1740.

Khan, M.A., et al., "iPSC-derived MSC therapy induces immune tolerance and supports long-term graft survival in mouse orthotopic tracheal transplants," Stem Cell Research & Therapy, 2019, 10(290):1-15.

Yang, H., et al., "Human induced pluripotent stem cell-derived mesenchymal stem cells promote healing via TNF-α-stimulated gene-6 in inflammatory bowel disease models," Cell Death and Disease, 2019, 10(718):1-16.

Cuascut, F.X., et al., "Stem Cell-Based Therapies for Multiple Sclerosis: Current Perspectives," Biomedicines, 2019, 7(26):1-13.

Guilak, F., et al., "Designer Stem Cells: Genome Engineering and the Next Generation of Cell-Based Therapies," Journal of Orthopaedic Research, 2019, 37:1287-1293.

D'Antonio, M., et al., "High-Throughput and Cost-Effective Characterization of Induced Pluripotent Stem Cells," Stem Cells Reports, 2017, 8:1101-1111.

Li, W., et al., "Radix Rehmanniae Extract Ameliorates Experimental Autoimmune Encephalomyelitis by Surpressing Macrophage-Derived Nitrative Damage," Frontiers in Physiology, 2018, 9(864):1-13.

Stromnes, I.M., et al., "Active induction of experimental allergic encephalomyelitis," Nature Protocols, 2006, 1(4):1810-1819.

Wu, H., et al., "Caveolin-1 is Critical for Lymphocyte Trafficking into Central Nervous System during Experimental Autoimmune Encephalomyelitis," The Journal of Neuroscience, 2016, 36(19):5193-5199.

Ksiazek, K., "A Comprehensive Review on Mesenchymal Stem Cell Growth and Senescence," Rejuvenation Research, 2009, 12(2):105-116.

Trento, C., et al., "Mesenchymal stem cells and innate tolerance: biology and clinical applications," Swiss Medical Weekly, 2010, 140:1-6.

Ng, F., et al., "PDGF, TGF-β, and FGF signaling is important for differentiation and growth of mesenchymal stem cells (MSCs): transcriptional profiling can identify markers and signaling pathways important in differentiation of MSCs into adipogenic, chondrogenic, and osteogenic lineages," Blood, 2008, 112(2):295-307.

Sackstein, R., et al., "Ex vivo glycan engineering of CD44 programs human multipotent mesenchymal stromal cell trafficking to bone," Nature Medicine, 2008, 14(2):181-187.

Liu, B., et al., "Enhanced tumor growth inhibition by mesenchymal stem cells derived from iPSCs with targeted integration of interleukin24 into rDNA loci," Oncotarget, 2017, 8(25):40791-40803.

Chen, S., et al., "Hepatocyte growth factor-modified mesenchymal stem cells improve ischemia reperfusion-induced acute lung injury in rats," Gene Therapy accepted article preview, 2016, pp. 1-37.

Friedenstein, A.J., et al., "The Development of Fibroblast Colonies in Monolayer Cultures of Guinea-Pig Bone Marrow and Spleen Cells," Cell Tissue Kinet., 1970, 3:393-403.

Kaji, K., et al., "Virus-free induction of pluripotency and subsequent excision of reprogramming factors," Nature, 2009, 458:1-6.

Kato, A., et al., "Assignment of the human α2-plasmin inhibitor gene (PLI) to chromosome region 18p11.1→q11.2 by in situ hybridization," Cytogenet Cell Genet., 1988, 47:209-211.

Takahashi, K., et al., "Induction of Pluripotent Stem Cells from Mouse Embryonic and Adult Fibroblast Cultures by Defined Factors," Cell, 2006, 126:663-676.

* cited by examiner

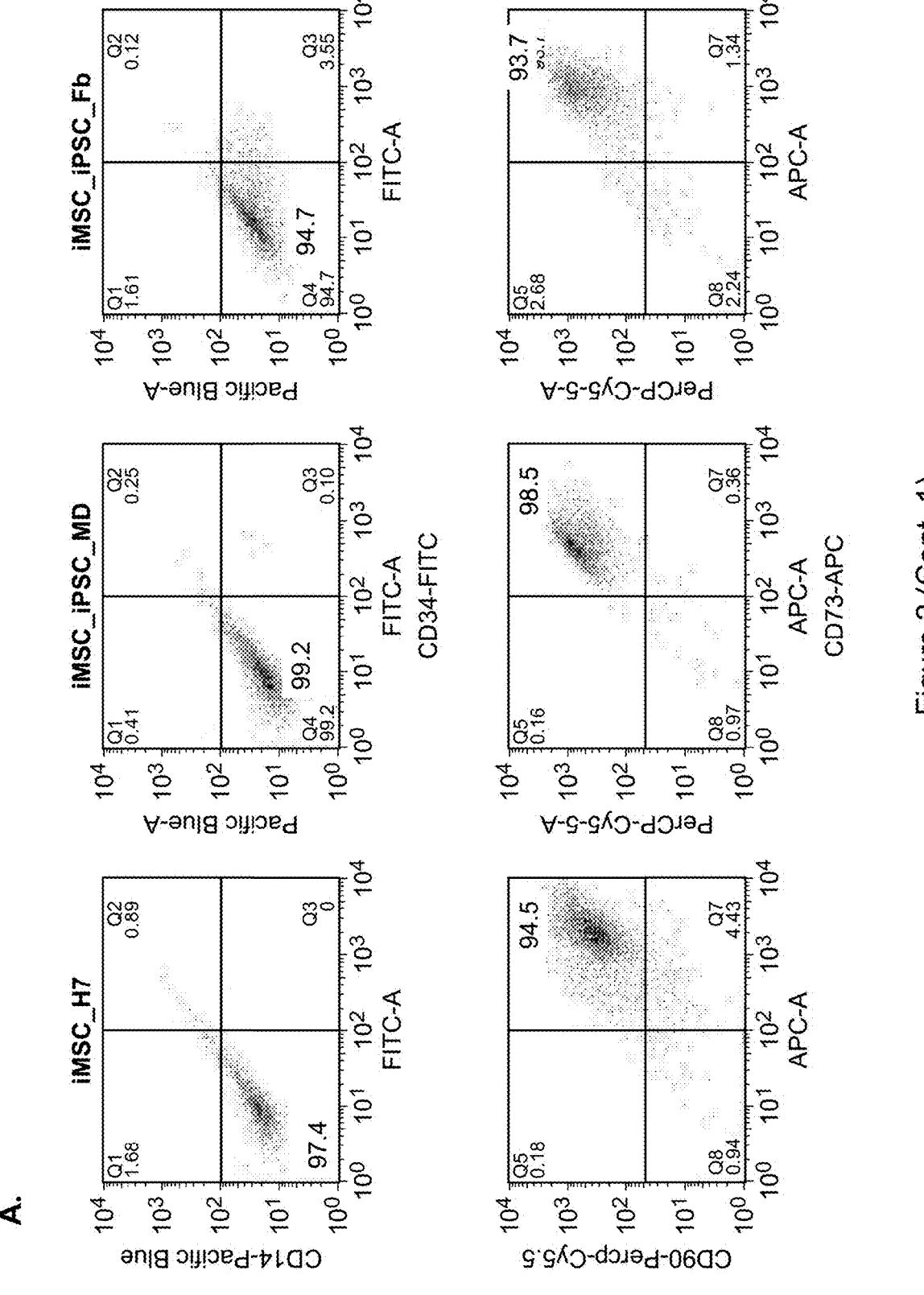
Figure 2 (Cont. 1)

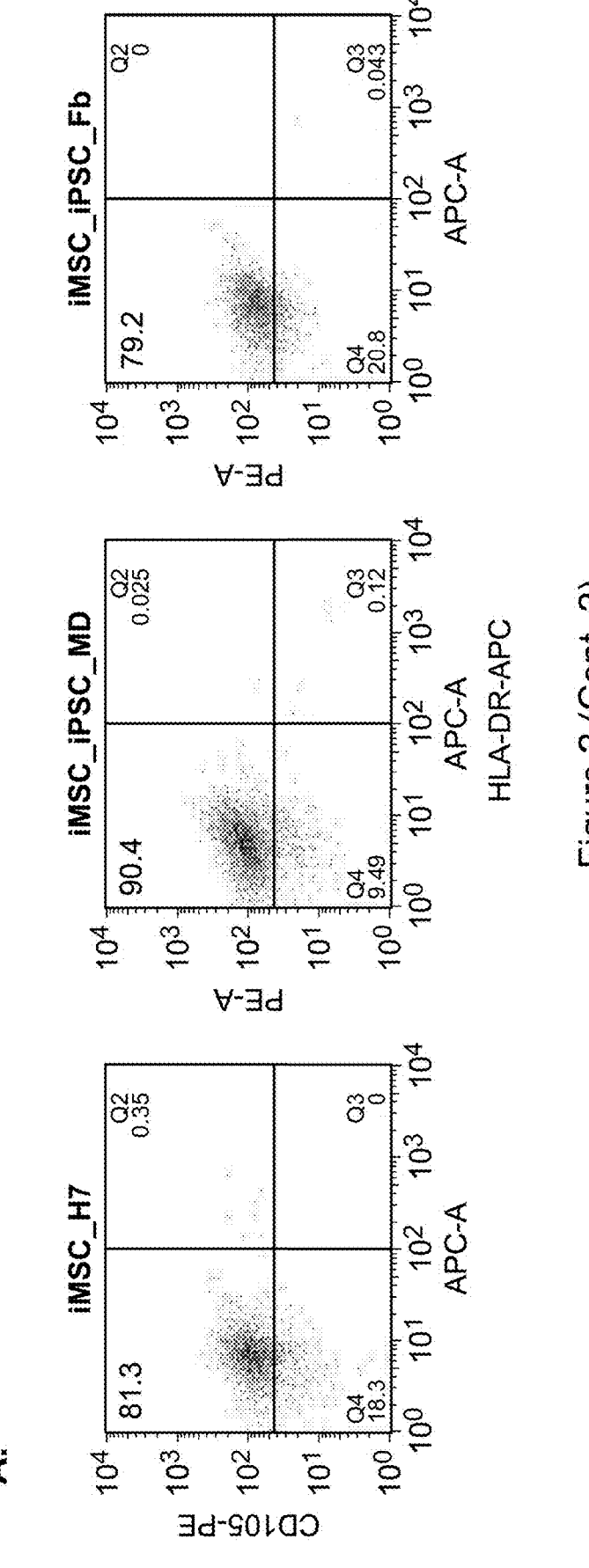
Figure 2 (Cont. 2)

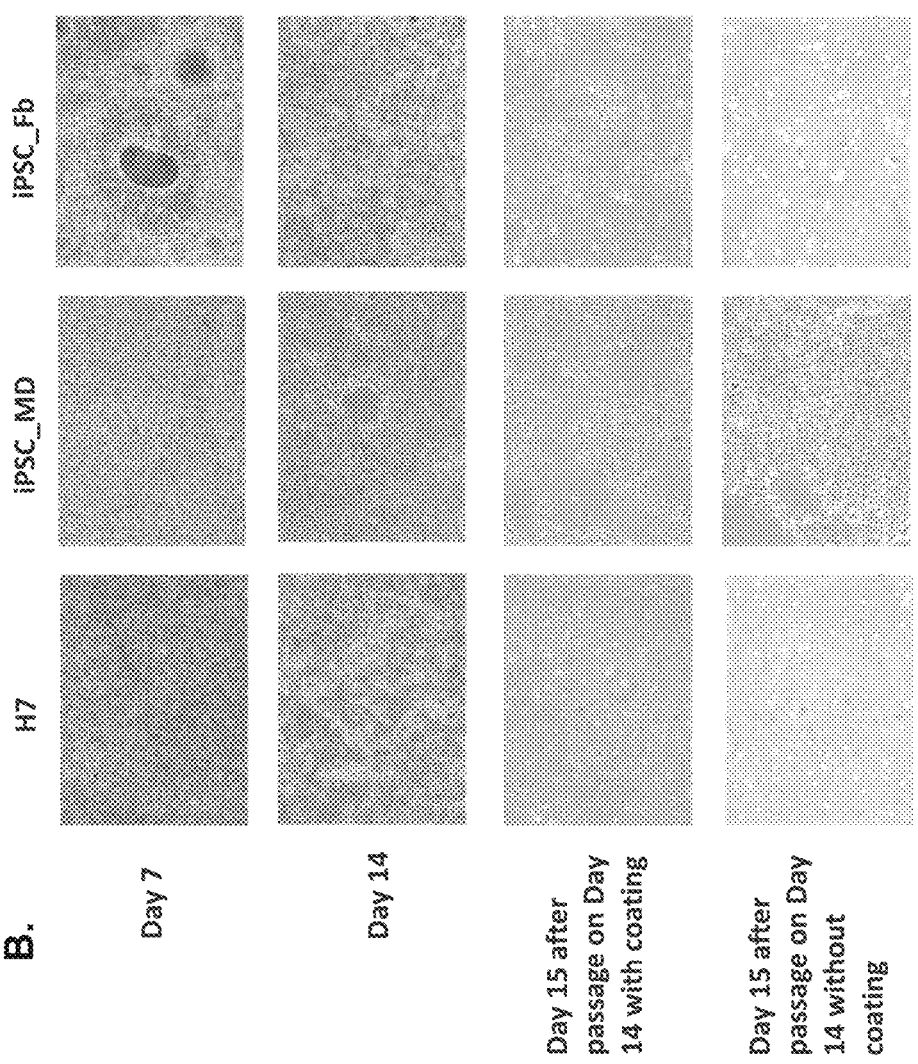
Figure 2 (Cont. 3)

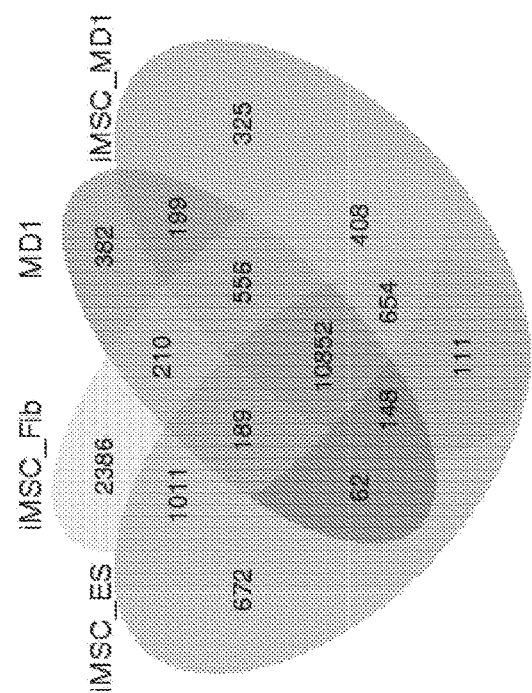
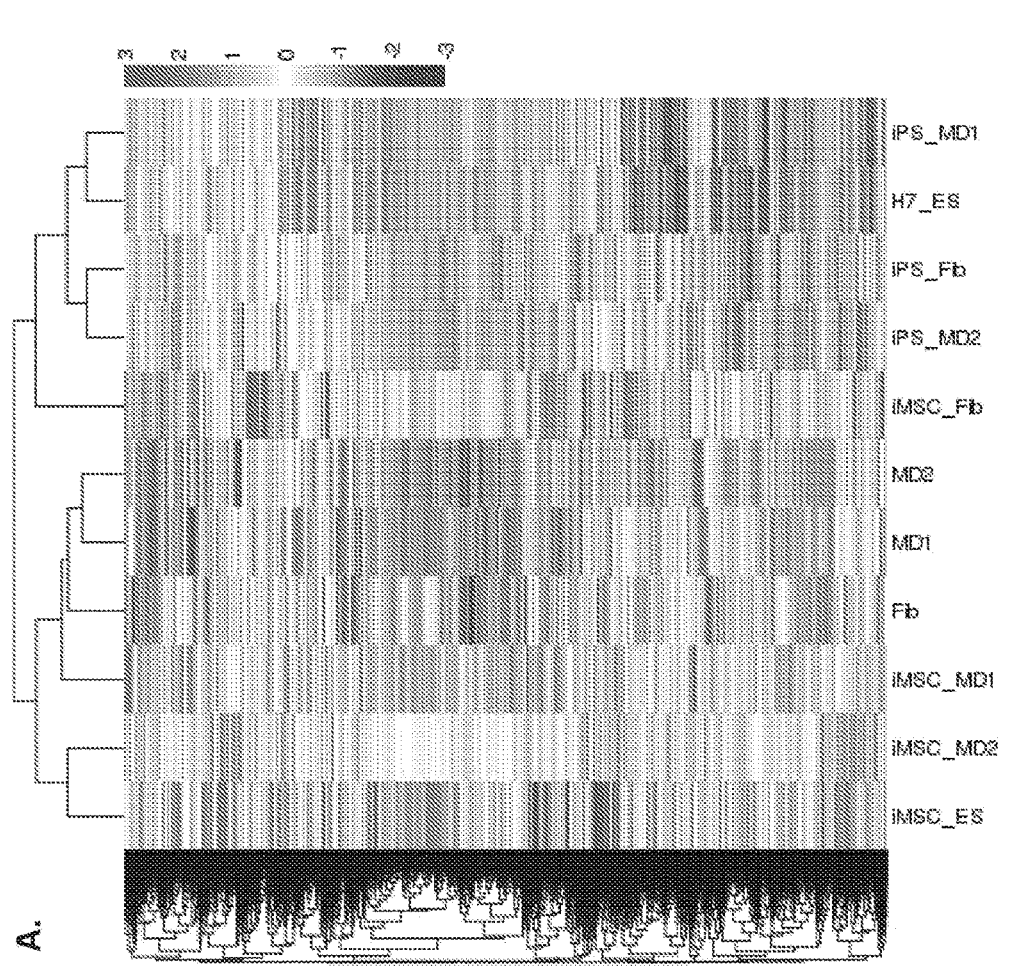
Figure 3

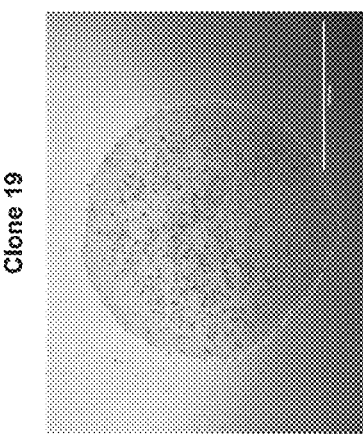
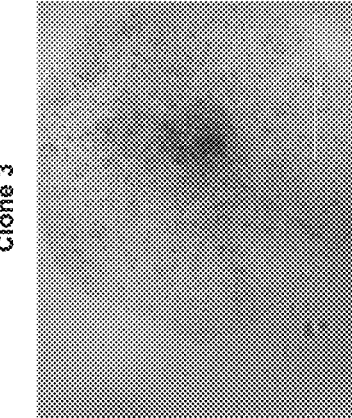
Figure 6

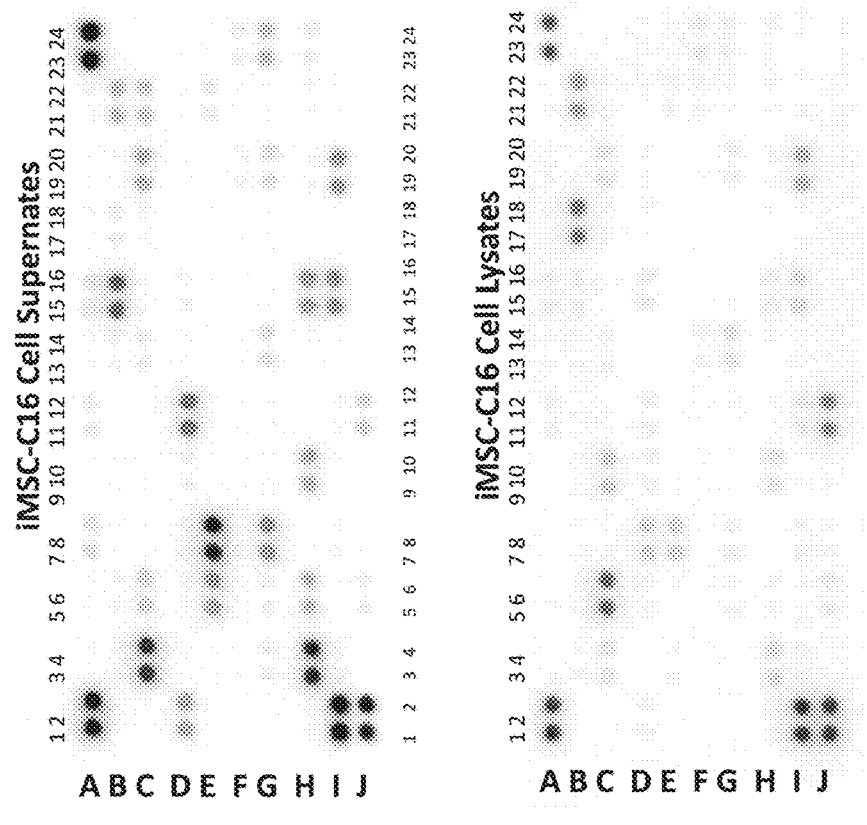
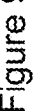
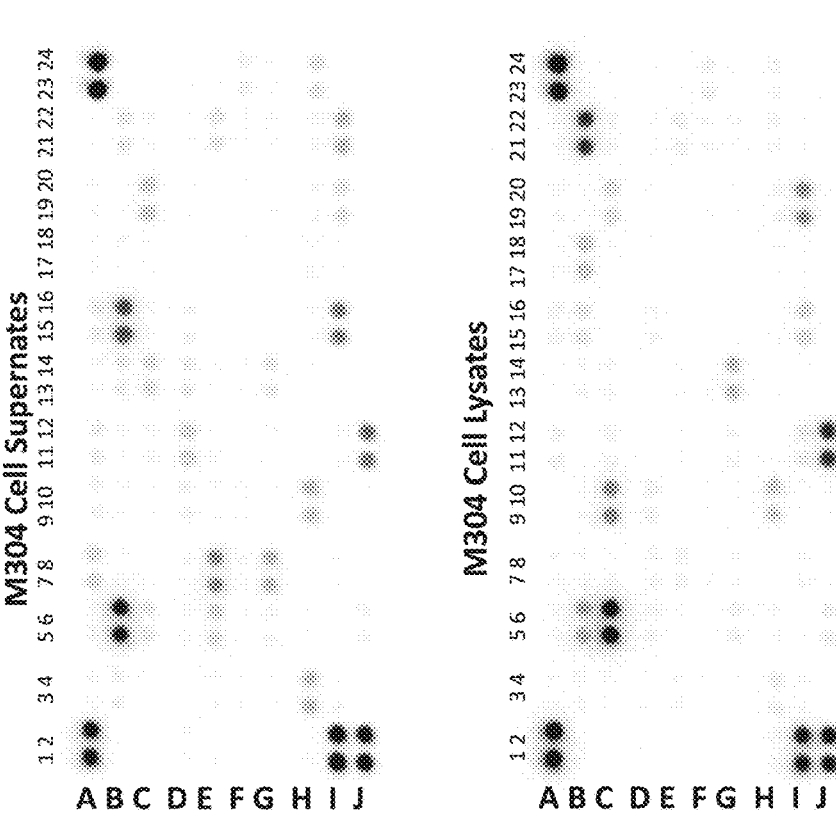
Figure 9

PBS

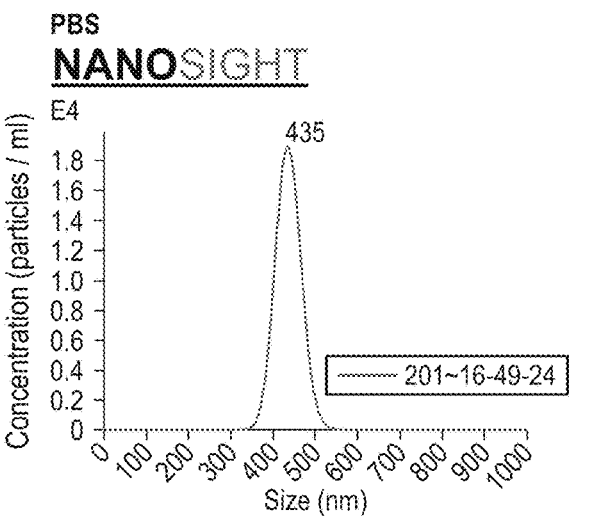

FTLA Concentration / Size graph for Experiment: 20180913-pbs 2018-09-13 16-49-12

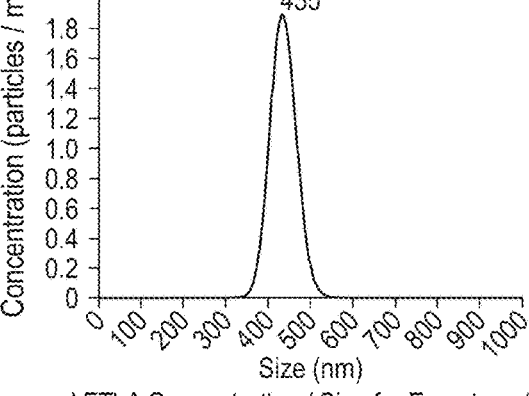

Averaged FTLA Concentration / Size for Experiment: 20180913-pbs 2018-09-13 16-49-12
Error bars indicate + / -1 standard error of the mean

Included Files

20180913-pbs 2018-09-13 16-49-24

Details

| | |
|---|---|
| NTA Version: | NTA 3.3 Dev Build 3.3.104 |
| Script Used: | SOP Standard Measurement 04-49-12PM 13~ |
| Time Captured: | 16:49:12 13/09/2018 |
| Operator: | |
| Pre-treatment: | |
| Sample Name: | |
| Diluent: | |
| Remarks: | |

Capture Settings

| | |
|---|---|
| Camera Type: | sCMOS |
| Laser Type: | Blue405 |
| Camera Level: | 16 |
| Slider Shutter: | 1300 |
| Slider Gain: | 512 |
| FPS | 25.0 |
| Number of Frames: | 1498 |
| Temperature: | 21.7 °C |
| Viscosity: | (Water) 1.0 cP |
| Dilution factor: | Dilution not recorded |

Analysis Settings

| | |
|---|---|
| Detect Threshold: | 5 |
| Blur Size: | Auto |
| Max Jump Distance: | Auto: 14.3 pix |

Results

Stats: Merged Data

| | |
|---|---|
| Mean: | 436.3 nm |
| Mode: | 434.0 nm |
| SD: | 30.4 nm |
| D10: | 379.9 nm |
| D50: | 435.5 nm |
| D90: | 475.6 nm |

Stats: Mean +/- Standard Error

| | |
|---|---|
| Mean: | 436.3 +/- 0.0 nm |
| Mode: | 434.0 +/- 0.0 nm |
| SD: | 30.4 +/- 0.0 nm |
| D10: | 397.9 +/- 0.0 nm |
| D50: | 435.5 +/- 0.0 nm |
| D90: | 475.6 +/- 0.0 nm |
| Concentration: | 1.43e+06 +/- 0.00e+00 particles/ml |
| | 0.1 +/- 0.0 particles/frame |
| | 0.1 +/- 0.0 centres/frame |

Figure 10

DMEM-LG+10%FBS (1000x)

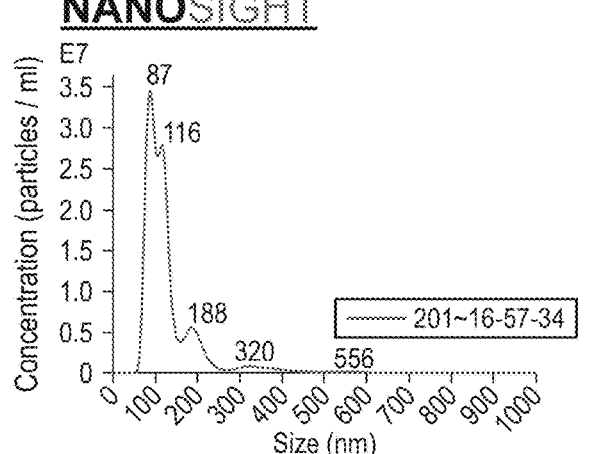

FTLA Concentration / Size graph for Experiment:
20180913-margaret 2018-09-13 16-57-15

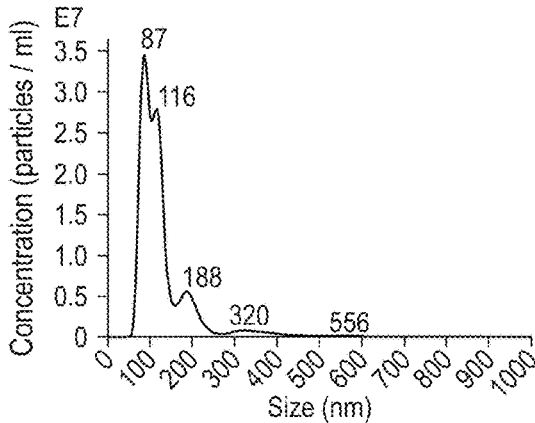

Averaged FTLA Concentration / Size for Experiment:
20180913-margaret 2018-09-13 16-57-15
Error bars indicate + / -1 standard error of the mean

| Included Files | Results |
|---|---|
| 20180913-margaret 2018-09-13 16-57-34 | Stats: Merged Data |
| Details | Mean:    126.7 nm |
| | Mode:    86.9 nm |
| NTA Version:    NTA 3.3 Dev Build 3.3.104 | SD:    64.6 nm |
| Script Used:    SOP Standard Measurement | D10:    78.7 nm |
|    04-57-15PM 13~ | D50:    109.3 nm |
| Time Captured:    16:57:15 13/09/2018 | D90:    195.0 nm |
| Operator: | |
| Pre-treatment: | Stats: Mean +/- Standard Error |
| Sample Name: | Mean:    126.7 +/- 0.0 nm |
| Diluent: | Mode:    86.9 +/- 0.0 nm |
| Remarks: | SD:    64.6 +/- 0.0 nm |
| Capture Settings | D10:    78.7 +/- 0.0 nm |
| | D50:    109.3 +/- 0.0 nm |
| Camera Type:    sCMOS | D90:    195.0 +/- 0.0 nm |
| Laser Type:    Blue405 | Concentration:    2.31e+09 +/- 0.00e+00 |
| Camera Level:    13 |    particles/ml |
| Slider Shutter:    1232 |    117.1 +/- 0.0 particles/frame |
| Slider Gain:    219 |    114.3 +/- 0.0 centres/frame |
| FPS    25.0 | |
| Number of Frames:    1498 | |
| Temperature:    21.8 °C | |
| Viscosity:    (Water) 1.0 cP | |
| Dilution factor:    Dilution not recorded | |
| Analysis Settings | |
| Detect Threshold:    4 | |
| Blur Size:    Auto | |
| Max Jump Distance:    Auto: 12.6 pix | |

Figure 10 (Cont. 1)

iMSC-CM

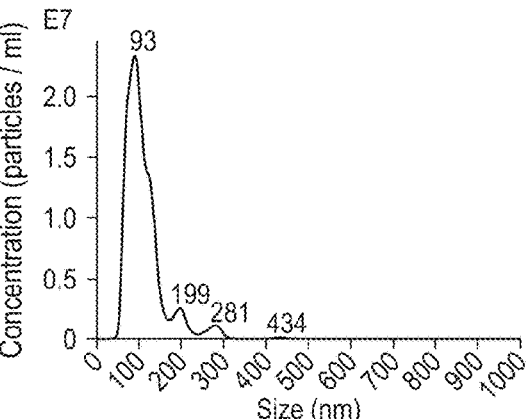

NANOSIGHT

FTLA Concentration / Size graph for Experiment:
iMSC-dilute-1-500 2018-06-29 14-03-30 iMSC-dilute-1-500 2018-06-29 14-03-30

Averaged FTLA Concentration / Size for Experiment:
iMSC-dilute-1-500 2018-06-29 14-03-30
Error bars indicate + / -1 standard error of the mean

| Included Files | | Results | |
|---|---|---|---|
| iMSC-dilute-1-500 2018-06-29 14-03-42 | | Stats: Merged Data | |
| Details | | Mean: | 113.0 nm |
| | | Mode: | 92.1 nm |
| NTA Version: | NTA 3.3 Dev Build 3.3.104 | SD: | 46.2 nm |
| Script Used: | SOP Standard Measurement 02-03-30PM 29J~ | D10: | 71.3 nm |
| | | D50: | 101.4 nm |
| Time Captured: | 14:03:30 29/06/2018 | D90: | 166.6 nm |
| Operator: | | | |
| Pre-treatment: | | Stats: Mean +/- Standard Error | |
| Sample Name: | | Mean: | 113.0 +/- 0.0 nm |
| Diluent: | | Mode: | 92.1 +/- 0.0 nm |
| Remarks: | | SD: | 46.2 +/- 0.0 nm |
| Capture Settings | | D10: | 71.3 +/- 0.0 nm |
| | | D50: | 101.4 +/- 0.0 nm |
| Camera Type: | sCMOS | D90: | 166.6 +/- 0.0 nm |
| Laser Type: | Blue405 | Concentration: | 1.63e+09 +/- 0.00e+00 |
| Camera Level: | 14 | | particles/ml |
| Slider Shutter: | 1259 | | 82.6 +/- 0.0 particles/frame |
| Slider Gain: | 366 | | 89.0 +/- 0.0 centres/frame |
| FPS | 25.0 | | |
| Number of Frames: | 1498 | | |
| Temperature: | 22.4 °C | | |
| Viscosity: | (Water) 0.9 cP | | |
| Dilution factor: | Dilution not recorded | | |
| Analysis Settings | | | |
| Detect Threshold: | 5 | | |
| Blur Size: | Auto | | |
| Max Jump Distance: | Auto: 14.1 pix | | |

Figure 10 (Cont. 2)

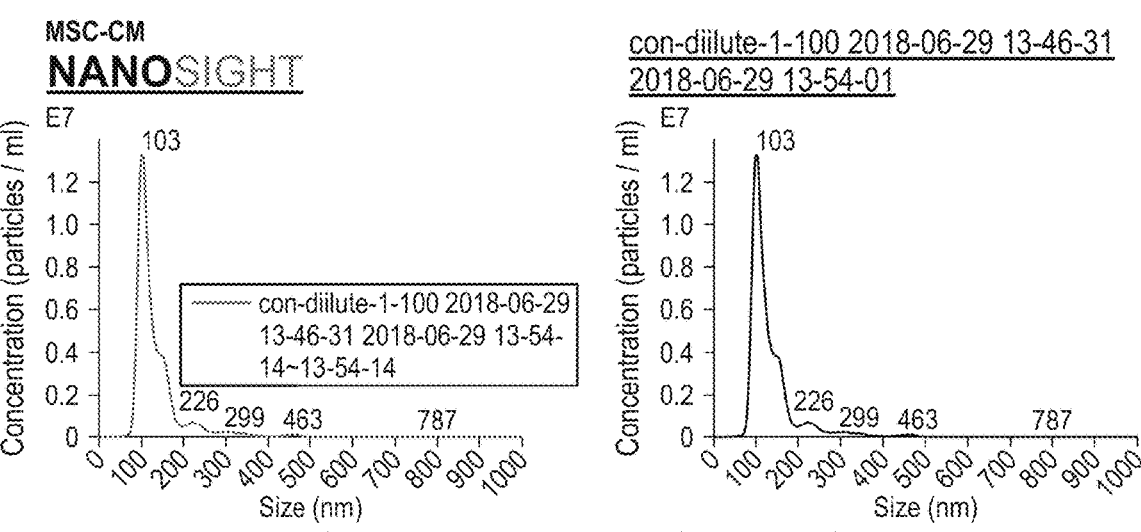

FTLA Concentration / Size graph for Experiment: con-dilute-1-100 2018-06-29 13-46-31 2018-06-29 13-54-01

Averaged FTLA Concentration / Size for Experiment: con-dilute-1-100 2018-06-29 13-46-31 2018-06-29 13-54-01 Error bars indicate + / -1 standard error of the mean

Included Files con-dilute-1-100 2018-06-29 13-46-31 2018-06-29 13-54-14

Details

| | |
|---|---|
| NTA Version: | NTA 3.3 Dev Build 3.3.104 |
| Script Used: | SOP Standard Measurement 01-54-01PM 29J~ |
| Time Captured: | 13:54:01 29/06/2018 |
| Operator: | |
| Pre-treatment: | |
| Sample Name: | |
| Diluent: | |
| Remarks: | |

Capture Settings

| | |
|---|---|
| Camera Type: | sCMOS |
| Laser Type: | Blue405 |
| Camera Level: | 13 |
| Slider Shutter: | 1232 |
| Slider Gain: | 219 |
| FPS | 25.0 |
| Number of Frames: | 1498 |
| Temperature: | 22.1 °C |
| Viscosity: | (Water) 1.0 cP |
| Dilution factor: | Dilution not recorded |

Analysis Settings

| | |
|---|---|
| Detect Threshold: | 5 |
| Blur Size: | Auto |
| Max Jump Distance: | Auto: 12.2 pix |

Results

Stats: Merged Data

| | |
|---|---|
| Mean: | 135.2 nm |
| Mode: | 102.4 nm |
| SD: | 60.9 nm |
| D10: | 93.4 nm |
| D50: | 116.0 nm |
| D90: | 190.6 nm |

Stats: Mean +/- Standard Error

| | |
|---|---|
| Mean: | 135.2 +/- 0.0 nm |
| Mode: | 102.4 +/- 0.0 nm |
| SD: | 60.9 +/- 0.0 nm |
| D10: | 93.4 +/- 0.0 nm |
| D50: | 116.0 +/- 0.0 nm |
| D90: | 190.6 +/- 0.0 nm |
| Concentration: | 6.47e+08 +/- 0.00e+00 particles/ml 32.8 +/- 0.0 particles/frame 34.5 +/- 0.0 centres/frame |

Figure 10 (Cont. 3)

MESENCHYMAL STROMAL CELLS AS A REPROGRAMMING SOURCE FOR iPSC INDUCTION

CROSS-REFERENCE TO RELATED APPLICATIONS

This application is the U.S. national stage application of International Patent Application No. PCT/CN2020/132241, filed Nov. 27, 2020, which claims the benefit of U.S. Provisional Patent Application No. 62/941,843, filed Nov. 28, 2019, the disclosures of each of which are incorporated herein by reference in their entirety.

FIELD OF INVENTION

The present invention belongs to stem cell technology, and in particular relates to a method for generating induced mesenchymal stromal cells (iMSCs) from induced pluripotent stem cells (iPSCs), the iMSC generated by the method as well as the use thereof.

BACKGROUND OF INVENTION

Mesenchymal stem/stromal cells are multipotent cells. They were firstly found and described as a singular type of precursor cell within mesenchyme in 1924 [3] and their clonal nature of marrow cells was revealed in 1960s [4]. An ex vivo assay, colony-forming unit-fibroblasts (CFU-F), was established to examine clonogenic potential of these multi-potent marrow cells in 1968 [5]. Although MSCs are initially considered as hematopoietic supporting cells in bone marrow, their capabilities of self-renewal, and differentiation into multiple cell types, including adipocytes, osteoblasts and chondrocytes, were unveiled later [6, 7]. Allogeneic transplanted MSCs can evade immune rejection due to their immunosuppression potential [8]. And cytokines and chemokines secreted by MSCs showed immunomodulatory functions [9]. Therefore, MSCs become popular in cell therapy by direct injection of cells or indirect application of their conditional medium [7, 10, 11]. Up to now, more than 200 clinical trials have been started, but MSCs therapy is still in the safety stage of testing [12]. The two main obstacles for clinical applications of primary MSCs are the heterogeneity of the cultured cells and their limited ex vivo proliferative capacity. Immortalized MSCs and iPSC derived MSCs provide an attractive alternative for primary MSCs. They have unlimited or much higher ex vivo proliferative capacity than primary MSCs and thus can be expended to substantial amount for clinical applications [13, 14].

Induced pluripotent stem cells (iPSCs) can be reprogrammed from different cell types, such as fibroblasts and peripheral blood mononuclear cells (PBMCs). Cellular origin may influence lineage differentiation propensity of human iPSCs[1, 2]. iPSCs was firstly developed by Shinya Yamanaka who reprogrammed mouse adult fibroblasts in 2006 and reprogrammed human adult fibroblasts in 2007 by transducing 4 transcriptional factors (Oct3/4, Sox2, Klf4 and cMyc)[15, 16]. iPSCs are considered as pluripotent cells with similar stemness as embryonic stem cells. This invention created a new era for stem cell applications by solving ethical limitations on human embryonic stem cells. There are many different methods to deliver the reprogramming factors nowadays, which can be summarized in 3 strategies [17]: non-viral, integrating viruses, and nonintegrating viruses reprogramming methods. Non-viral reprogramming methods include mRNA transfection [18], miRNA infections/transfection [19-21], piggyBac transfection [22], mini-circle vectors [23] and episomal plasmids [24]. Non-viral approaches prevent the risk of viral integration into the host genome increasing the risk of tumorigenicity. However, the efficiency of most non-viral methods are lower than 0.05% [17]. With higher efficiency, lentiviral vectors are widely used for infecting nondividing and proliferating cells. But the major concern of this method is about incorporation of the lentiviral vector sequences into the iPSCs genome. Then nonintegrating viral vectors, Sendai virus vector for example, are developed to avoid genomic integration. Although it requires a virus removal step of about 10 passages, Sendai virus-based reprogramming has the highest efficiency which can reach 1% for fibroblasts and 0.1% for blood cells.

With these transduction methods, iPSCs are able to be derived from various cell types, including fibroblasts [15, 16], peripheral blood mononuclear cells (PBMCs) [25, 26], skin biopsy [27], mesenchymal stromal cells (MSCs) [28], keratinocytes from a single hair pluck [29] and renal epithelial cells in the urine [30-32]. iPSCs also have been induced into MSCs (iMSCs) [14, 33, 34], but the immuno-modulating functions of iMSCs were contradictory in some reports [35-37]. iMSCs have been considered as a convenient, efficient and commercial source for future cellular therapy [38, 39]. However, a systemic comparison on iMSCs derived from iPSCs of different origins has not been done yet.

DESCRIPTION OF THE INVENTION

In this disclosure, iPSCs were generated using Sendai virus with Yamanaka transcriptional factors. With different sources, the capabilities of iPSCs have been evaluated, including identification of specific markers, embryoid formation, teratoma formation and lineage differentiations. MSCs derived iPSCs showed advantages on differentiation into iMSCs compared to other sources, which confirmed by surface marker identification and gene expression profiling with RNA-seq. According to comparison of released cytokines, these iMSCs also maintained similar biological immunomodulating functions to primary MSCs both in vitro and in vivo. A stable hMSCs derived iPSC cell line was generated and an efficient expansion method for functional iMSCs ex vivo was established.

In a first aspect, the present disclosure provides a method for generating induced mesenchymal stromal cells (iMSCs) comprising:

culturing induced pluripotent stem cells (iPSCs) under a first medium for a first predetermined period;

replacing the first medium with a second medium and culturing the cells under the second medium for a second predetermined period;

trypsinizing the cultured cells;

seeding the trypsinized cells on a coated or non-coated tissue culture under a third medium for a third predetermined period; and replacing the third medium with a fourth medium and culturing the seeded cells for a fourth predetermined period.

In some embodiments, the iPSCs are generated by reprogramming human primary mesenchymal stromal cells (MSCs).

In some embodiments, the first medium may comprise:

a knockout serum; and a TGF beta and ALK inhibitor.

In some embodiments, the second medium may comprise:

a Dulbecco's Modified Eagle Medium: Nutrient Mixture F-12 (DMEM/F12);

a TGF beta and ALK inhibitor; and a knockout serum or an Insulin-Transferrin-Selenium (ITS-G) solution.

In some embodiments, the third medium may comprise: DMEM/F12;

a knockout serum; and a basic fibroblast growth factor (bFGF) and an epidermal growth factor (EGF).

In some embodiments, the fourth medium may comprise DMEM-LG medium and is optionally supplemented with FBS.

In a second aspect, the present disclosure provides a method for generating induced mesenchymal stromal cells (iMSCs) by differentiation of the iPSCs, wherein the iPSCs are generated by reprogramming mesenchymal stromal cells (iMSCs).

In a third aspect, the present disclosure provides a method for generating induced mesenchymal stromal cells (iMSCs) by differentiation of the iPSCs, wherein the iPSCs are generated by reprogramming mesenchymal stromal cells (iMSCs).

In some embodiments of the second aspect and the third aspect of the present disclosure, the MSCs used for generating iPSCs are primary MSCs, e.g. human primary MSCs.

In a fourth aspect, the present disclosure provides a medium for generating or inducing induced mesenchymal stromal cells (iMSCs) comprising:

a Dulbecco's Modified Eagle Medium: Nutrient Mixture F-12 (DMEM/F12);

a knockout serum; and a TGF beta and ALK inhibitor.

In some embodiments, the medium further comprises:

a cytokine; and an epidermal growth factor (EGF).

In some embodiments, the medium further comprises:

a bovine serum albumin; and an Insulin-Transferrin-Selenium (ITS-G) solution.

In a fifth aspect, the present disclosure provides an induced mesenchymal stromal cells (iMSCs) generated by the method of the first, the second or the third aspect of the disclosure.

In a sixth aspect, the present disclosure provides a composition comprising a plurality of the iMSC fifth aspect, and optionally a carrier, a excipient or a diluent.

In a seventh aspect, the present disclosure provides a method for treating a disease in a subject, comprising administrating an effective amount of the iMSC of the fifth aspect or the composition of the sixth aspect into the subject.

In an eighth aspect, the present disclosure provides the iMSC of the fifth aspect or the composition of the sixth aspect for use in treating a disease in a subject.

In a ninth aspect, the present disclosure provides the iMSC of the fifth aspect or the composition of the sixth aspect in the manufacture of a medicament for treating a disease in a subject.

In some embodiments of the seventh aspect, the eighth aspect and the ninth aspect of the present disclosure, the disease may be selected from an autoimmune disease and an inflammatory disease.

The present disclosure is the first to investigate the iMSCs in a systematic comparison, including specific surface markers, mRNA transcriptional levels and relative cytokine secretion. It is found that it's more efficient to induce iMSCs from iPSCs derived from BM MSCs than other cell sources, and these iMSCs are of better quality. These iMSCs can produce similar cytokines and chemokines as primary MSCs, and iMSC conditioned medium can be used for treatments in EAE model.

Although there were many reports with various methods to induce iPSCs into MSCs, TGF beta and ALK inhibitor SB431542 is widely used in the induction process combining with other cytokines, including bFGF, EGF and PDGF-AA. It is found primary MSCs can secret PDGF-AA and detectable in cell supernatant. In the protocol disclosed herein, PDGF-AA was not used for iMSC induction. Cytokines are secreted by MSCs and self-regulate their proliferation in culture, including EGF and FGF, HGF, IGF-1, PDGF, TGF-beta, and VEGF [45]. These factors are involved in the senescence-associated secretory phenotype (SASP) factors. Some of these SASP factor also play roles in inflammatory process, such as an immune-suppressive phenotype by high levels of soluble factors, including IDO, PGE2, TGP-beta, HGF and hemoxoygenase (HO) [46]. Ng and Tanavade proved that PDGF, TGF-beta, and FGF signaling is important for differentiation and growth of MSCs [47]. Therefore, it is considered that monitoring the level of some important cytokines are important for iMSC or primary MSC maintaining. Ingenuity Pathway Analysis (QIAGEN Bioinformatics) was used to analyze our RNA sequencing data with focusing on EGF, PDGF and TGF-beta pathways.

Furthermore, it is found under the same induction protocol, the iPSCs derived from BM MSCs presented advantages on iMSCs production with a higher CD44 expression level. Further specific CD44 neutralizing antibodies assay also showed that CD44 also impacted HGF secretion. CD44 is a cell surface glycoprotein involved in cell-cell interactions, cell adhesion and migration. Discrete sialofucosylation of CD44 turns it into a selectin-binding glycoform, which is usually observed on human hematopoietic stem cells and MSCs and functions as a bone marrow homing factor[48].

5 kinds of stem cells. (B) Comparison of the proliferation and survival during iMSCs induction and passage process. Although the proliferating status was similar during the iMSC induction, the survival and adherent percentage was much higher in iPSC-MD compared to the other two sources stem cells. With or without coating, iMSCs induced from iPSC-MD had a much higher survival rate. All experiments were triplicate. The experiments of iPSC-MD were repeated by using iPSCs derived from at least 2 donors.

FIG. 3. Comparison of the RNA expression levels among iMSCs from different sources. iMSC_MD1 and MD2 all showed more similar profile to primary MSCs. Sequencing reads are mapped back to human mRNA reference sequences, FRKM was used to present gene expression levels, and DESeq package was used for differential gene expression. Gene with an adjusted P-value <0.05 found by DESeq were assigned as differentially expressed.

Figure 4:
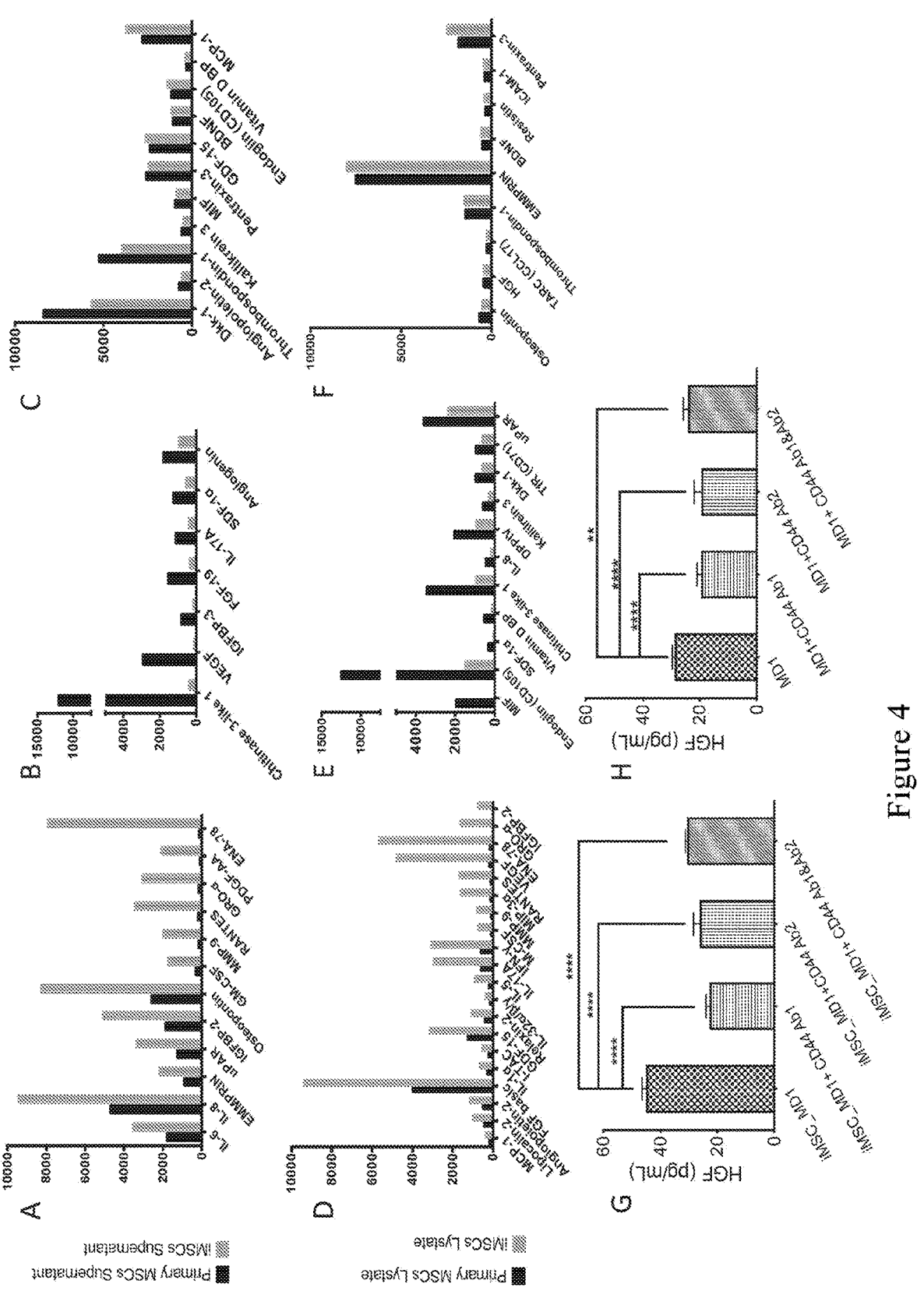

FIG. 4. Comparison of the protein profiles of secreted and cell lysate between primary MSCs and iMSCs_MD1. Levels of forty different soluble human protein were detected using Human XL cytokine array. Medium was combined 3 independent iMSC conditional medium. Results showed that secretion profiles were similar between the primary MSCs and iMSCs (from the same donor). They were summarized into 3 groups: (A) and (D) increased release or expression (>1.5 fold), or (B) and (E) decreased release or expression (<0.65 fold) or (C) and (F) relatively similar on release or expression (0.65<x<1.5 fold). (G) and (H) hepatocyte growth factor (HGF) in both iMSC_MD1 and primary MSCs MD1 was evaluated by using Human HGF ELISA kit. Meanwhile, the HGF secretion level was reduced after using CD44 neutralizing antibodies. Medium was changed after incubation with antibodies about 12 hrs and replaced with DMEM-LG+2% FBS for 12 hrs before supernatant collection (n=3).

Figure 5:
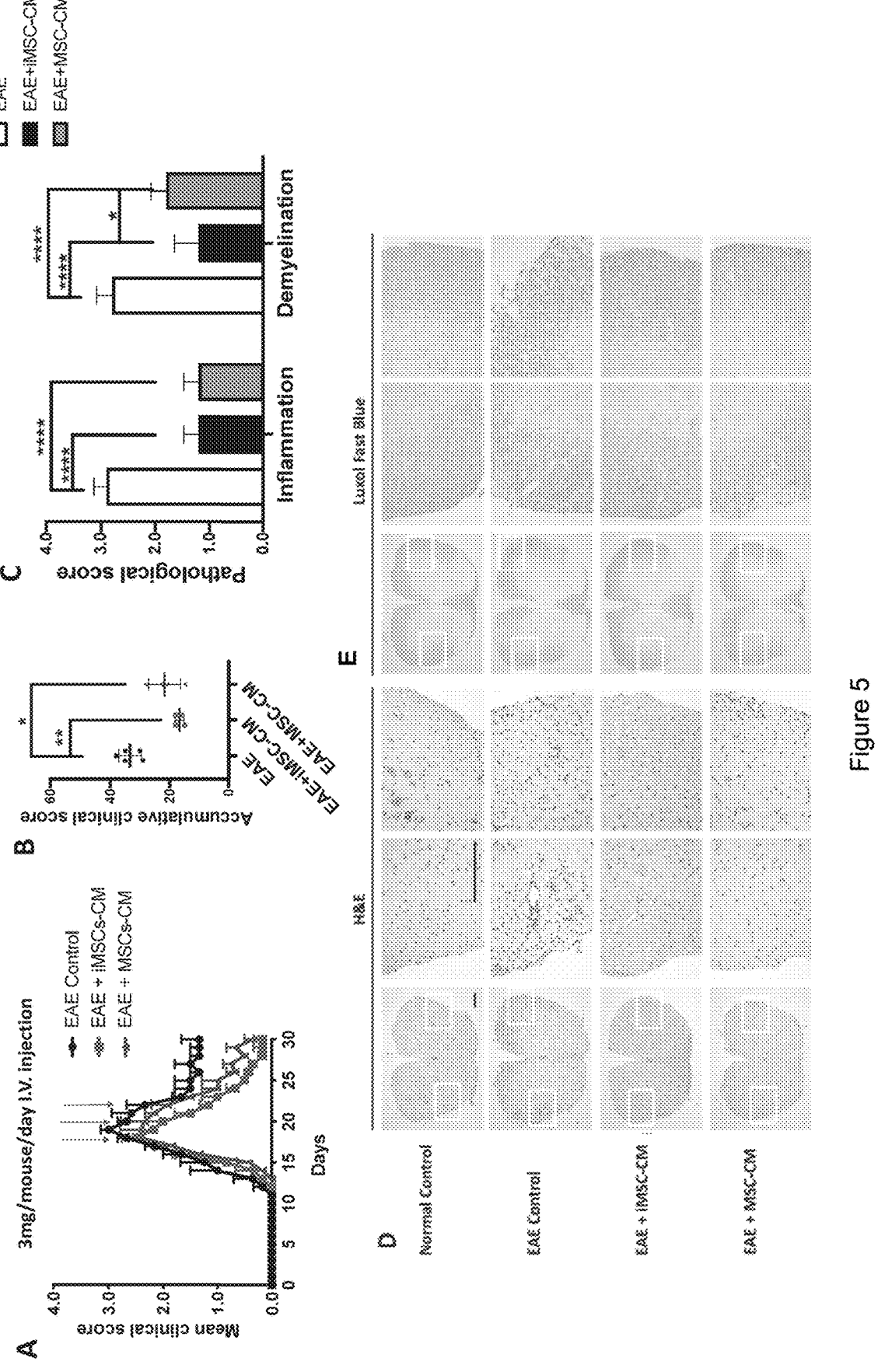

FIG. 5. HGF enriched conditional medium of iMSCs and MSCs ameliorated active EAE symptoms in treatment protocol (n=4-5) and inhibited inflammation and demyelination in the lumbar spinal cord of the EAE mice. Mice were administrated via i.g. with vehicle (n=5) or iMSC-CM treatment (n=4) or MSC-CM treatment (n=4) (3 mg/kg/day) once the other day starting from the day 18 of EAE induction, which reached the peak score (A). (B) Accumulative clinical scores of treatments for up till 30 dpi were calculated. Data presented as mean. Mean clinic scores were improved and demyelination and lymphocyte infiltration were reduced with both treatments compared to EAE mice. (C) Pathology scores of inflammation and demyelination for H7E and LFB images respectively. Lumbar spinal cords (L4-L6) from treated EAE mice with vehicle or CMs from iMSCs or MSCs were obtained at 30 dpi (3 mg/mouse/day) and stained by H&E (D) and Luxol Fast Blue (LFB) (E) (scale bar, 100 μm).

FIG. 6. Representative images of iPSC_MD cells (Passage 10) colony reprogrammed from hMSCs by Sendai viral transduction.

Figure 7:
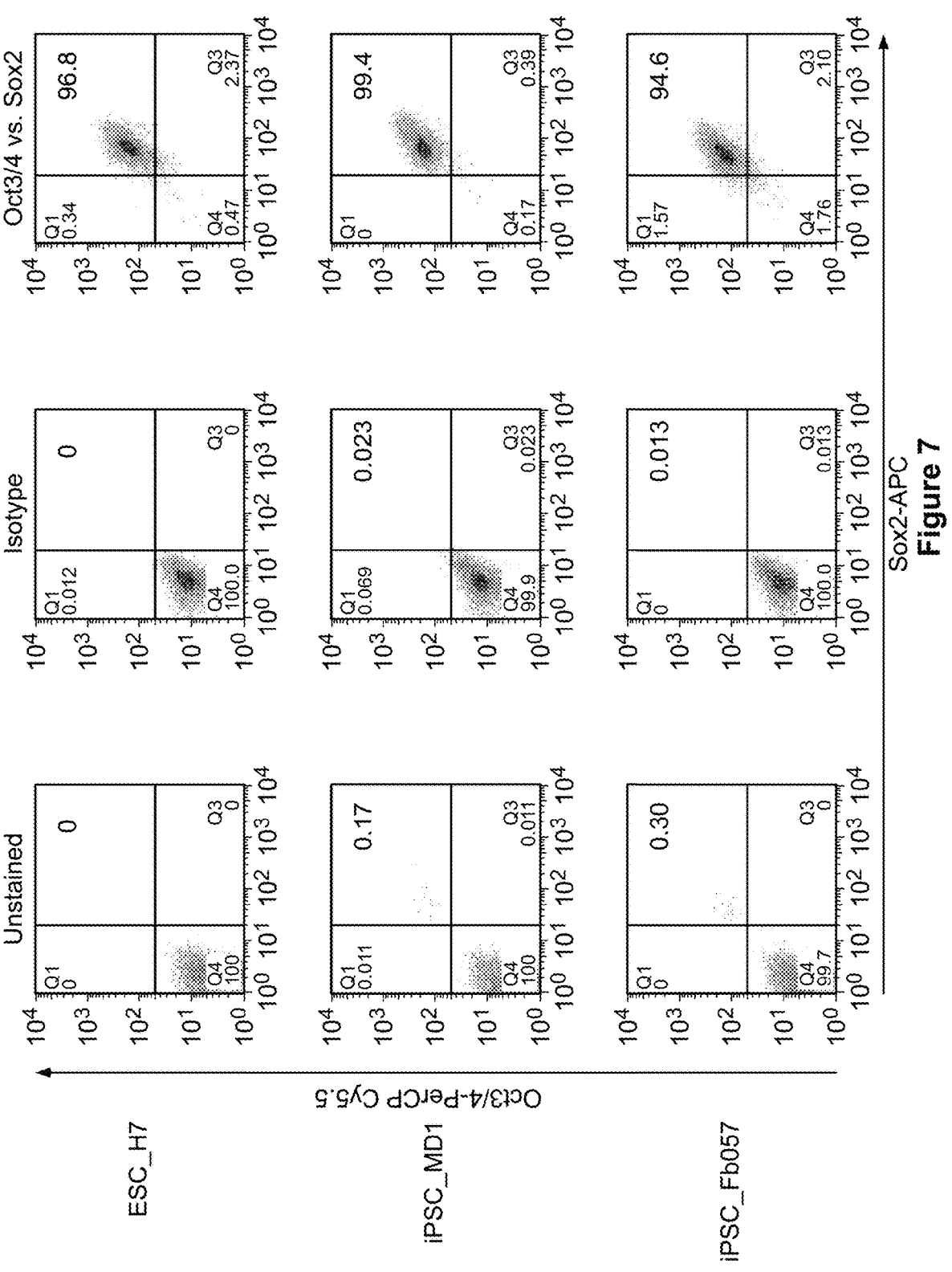
Figure 7:
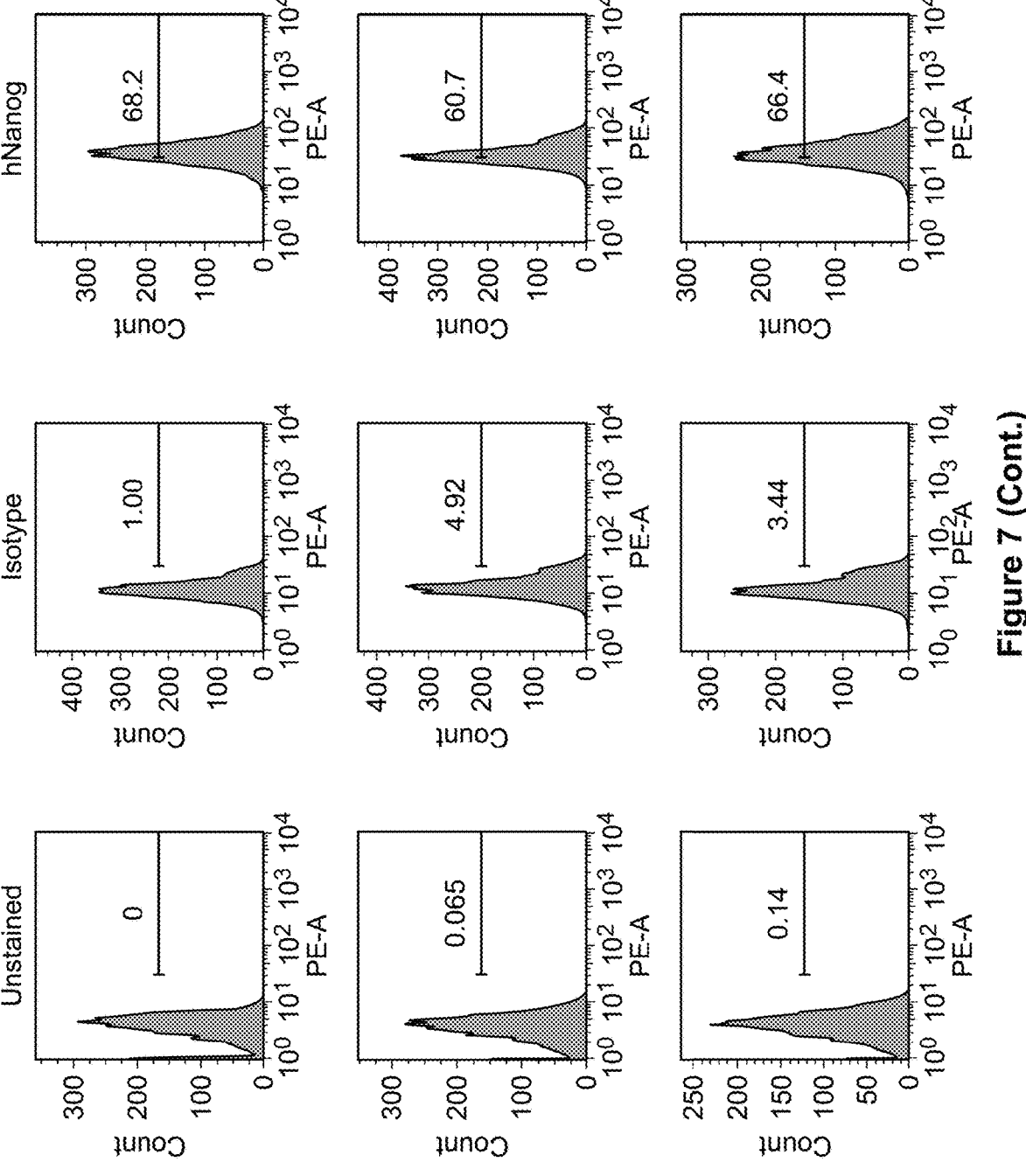

FIG. 7. Characterization of iPSCs specific markers and transcriptional factors by flowcytometry.

Figure 8:
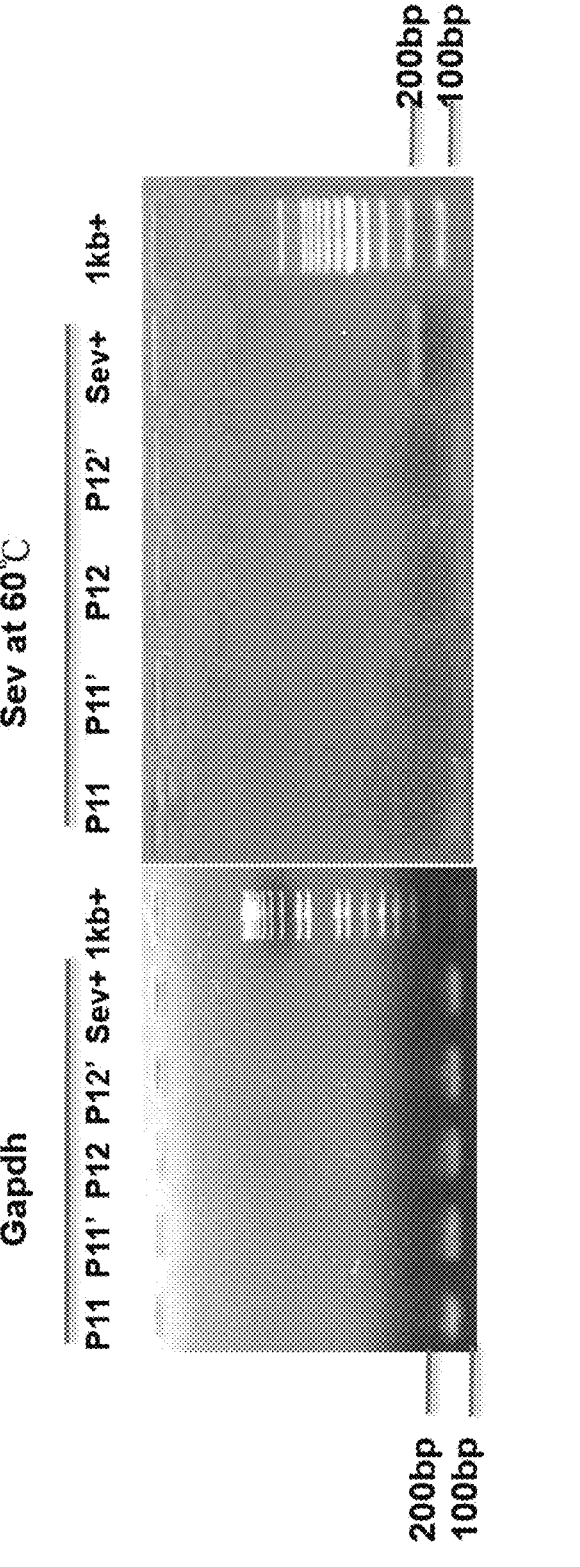

FIG. 8. Detection of clearance of Sendi virus by semi-PCR.

FIG. 9 and FIG. 10. Simple component size examination of conditional medium from iMSCs and MSCs by Nano-Sight NS300.

Figure 11:
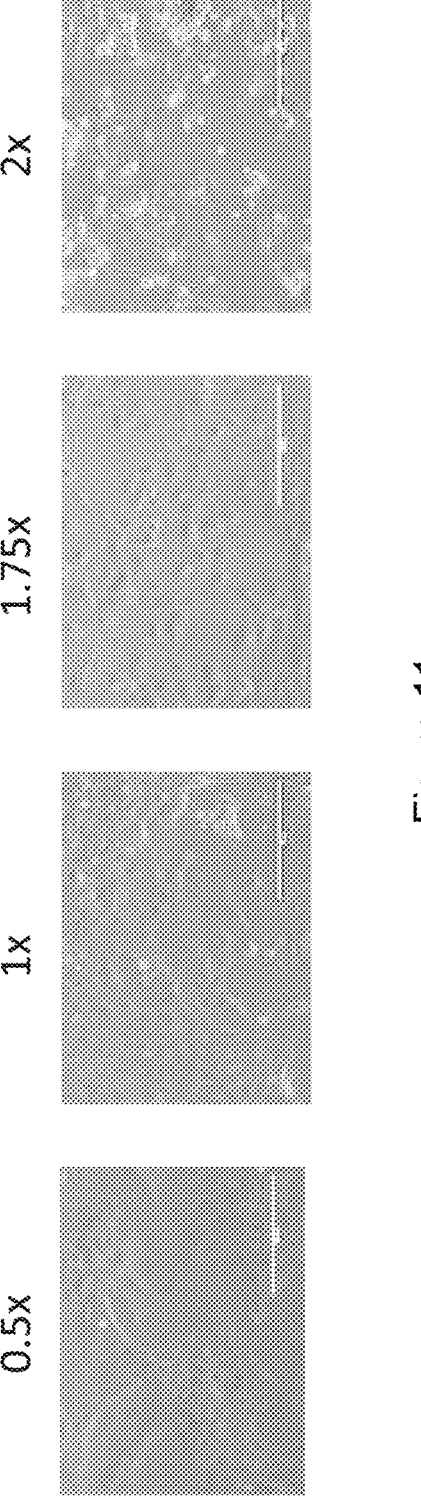

FIG. 11. Representative images of cells under different MOI of viral transfection. 1.75×MOI: KOS MOI=8.75, hc-Myc MOI=8.75, hKlf4 MOI=4.5; 2×MOI: KOS MOI=10, hc-Myc MOI=10, hKlf MOI=6).

6

Figure 12:
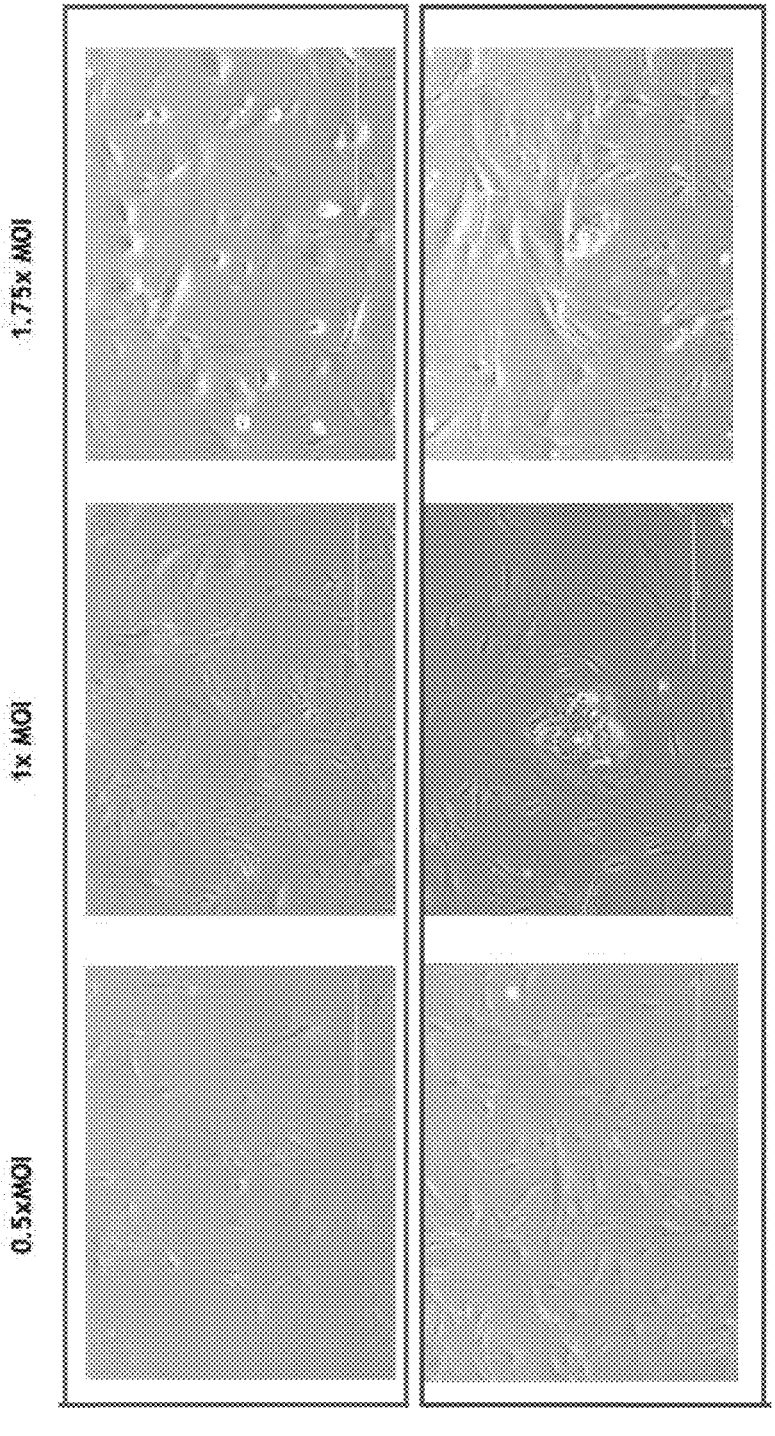

FIG. 12. Representative images of cells under different MOI and medium change strategies. Gradient 1: Day 9 change: 50% of (DMEM-LG with 10% FBS)+50% of E8 medium; Day 10 change: 100% of E8 medium. Gradient 2: Day 9 change: 70% of (DMEM-LG with 10% FBS)+30% of E8 medium; Day 10 change: 30% of (DMEM-LG with 10% FBS)+70% of E8 medium; Day 11 change: 100% of E8 medium.

EXAMPLES

The following examples serve to provide further appreciation of the invention but are not meant by any way to restrict the effective scope of the invention.

Example 1. Reprogramming Human MSCs into iPSCs

To compare characteristic of iMSCs derived from ES cells or iPSCs of different origins, one human ES cell line (H7) and two iPSC cell lines were included. The two iPSC cell lines are derived from human fibroblast (iPSC_Fb) and human primary bone marrow derived MSCs (iPSC_MD). iPSC_Fb was established previously, and human primary bone marrow derived MSCs were reprogrammed in this study (FIG. 6).

These MSC derived iPSCs (iPSC_MD) were characterized with different specific markers, including stem cell surface markers SEEA4, TRA-1-60 and TRA-1-81, as well as transcriptional factors SOX2 and OCT4 (FIG. 1(A) and FIG. 7). After Sendai virus was excluded at passages 11 in vitro (FIG. 8), the iPSC_MD cells were injected into C.B-17/Icr-scid-bg (SCID Beige) mice, and formation of well-encapsulated cystic tumors that harbored differentiated elements of all three primary embryonic germ layers was observed (FIG. 1(B)). All three germ layers can be found within embryoid bodies formed by iPSC_MD cells with corresponding marker genes expressed (FIGS. 1(C) and 1(D)). It was also checked that iPSC_MD cells had normal karyotypes using chromosomal microarray (FIG. 1(E)). These data indicated therefore that iPSCs cell lines have been established derived from hMSCs. One representative iPSC_MD cell line C16 was used for the following experiments.

Example 2. Derivation of MSC-Like Cells from Human iPSCs and ESCs (iMSCs)

Figure 2:
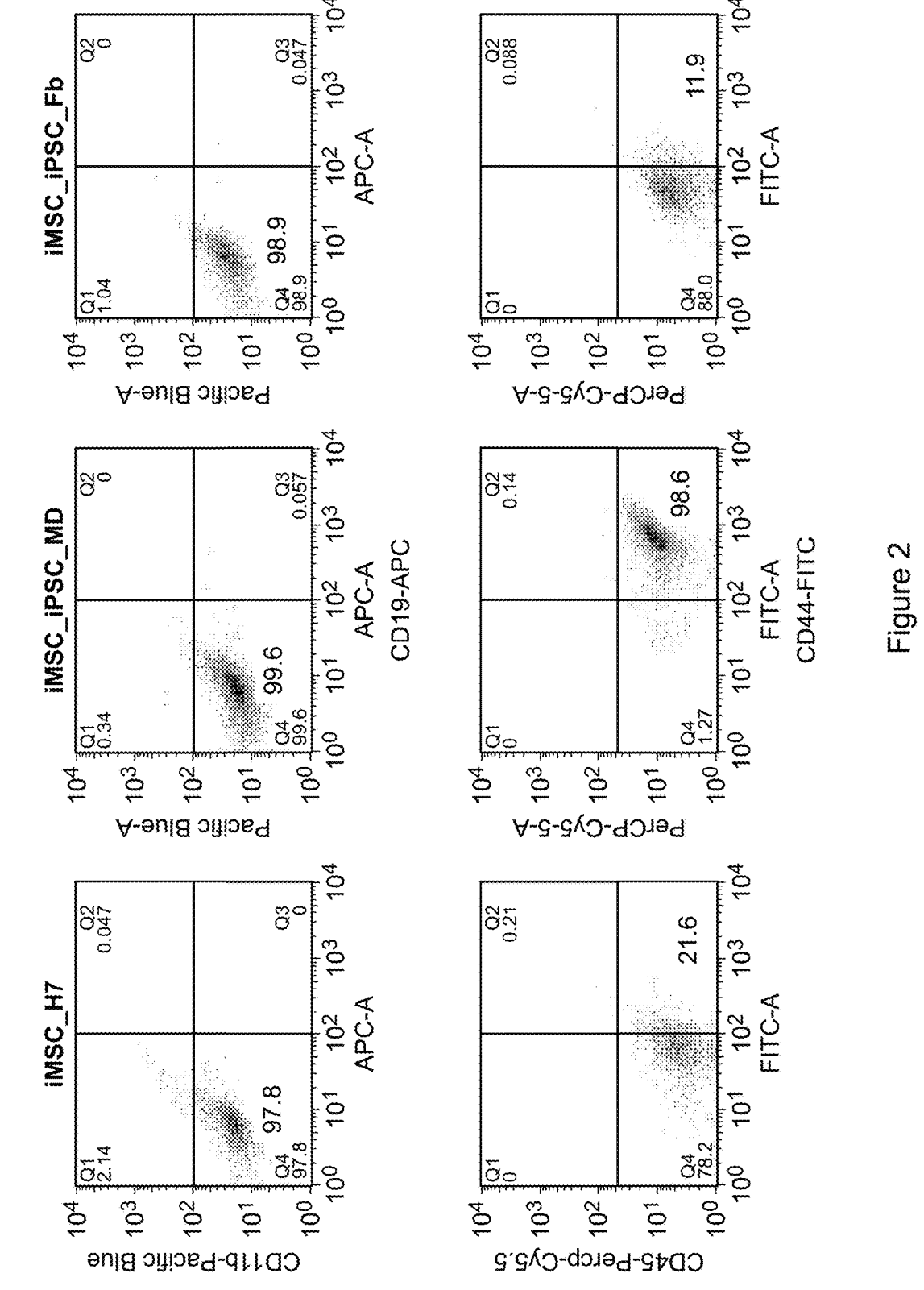
FIG. 2. Characterization of iMSCs. (A) Cell surface marker evaluation was performed for the presence of the typical MSC markers, including CD73$^+$, CD90$^+$, CD105$^+$ and CD44$^+$ while CD14$^-$, CD19$^-$, CD45$^-$ and HLA-DR$^-$. The expressions of most markers were similar, but CD44 present higher in iMSC-MD compared to the other two

Induced pluripotent stem cells can be further induced into MSC-like cells by inhibiting of TGF-β signaling pathway combined with growth factors EGF and bFGF. A simplified protocol was developed herein and ESCs (H7) and iPSCs (iPSC_MD and iPSC_Fb) were induced to differentiate into MSC-like cells (iMSCs). ESCs and iPSCs derived iMSCs were characterized with specific surface markers by flow cytometry after the 22-day differentiate protocol and all three iMSCs presented correct MSC surface marker profile, which were CD44+, CD90+, CD73+ and CD105+ while CD11b−, CD19−, CD45−, CD14−, HLA-DR− (FIG. 2(A)). GelTrex coated wells were used for the differentiation procedure. iMSCs derived from iPSC_MD (iMSC_iPSC_MD) presented much better cell morphology and higher CD44 level. CD44, a cell surface glycoprotein involved in cell adhesion, migration and intercellular interactions, was significant higher expressed in iMSC_iPSC_MD. Therefore, it was further investigated the survival rate and efficiency on cell passages, by comparing seeding cells on the GelTrex coated or non-Geltrex coated wells. With higher CD44 expressed, iMSC_iPSC_MD had higher survival rate and efficiency during passage (FIG. 2(B)).

To further compare gene expression profiles of the ESCs, iPSCs, and iMSCs involved in this study, transcriptomes of these cell lines were analyzed using RNAseq. He and hierarchical gene clustering shown iMSC_iPSC_MD cells had more similar profile to the primary MSCs (FIG. 3). Furthermore, the differentiation genes of ESCs, iPSCs derived from MSCs and fibroblasts, and their differentiated iMSCs and the primary MSCs were compared (FIG. 3).

Example 3. iMSC Secreted Functional Factors as Similar as Primary MSC

It is aimed to investigate the immune modulation effect of iMSCs_iPSC_MD on cytokine release and expression profiles (FIG. 3). In order to compare the protein profiles of secreted and cell lysate between primary MSCs and iMSCs, cells from the same donor were used to reduce the noise background as well as unexpected variants due to individual differences. Forty different soluble human proteins levels were detected by using Human XL cytokine array. Results showed that secretion profiles were similar between the primary MSCs and iMSCs. They were summarized into 3 groups (FIG. 4(A-F)), which were increasing release or expression (>1.5 fold) or decreasing release or expression (<0.65 fold) or relatively similar on release or expression (0.65<x<1.5 fold).

For released cytokines, 12 kinds of cytokines were enhanced releasing by iMSCs while 11 kinds of cytokines were reduced releasing by iMSCs. For cytokines in cell lysates, 20 kinds of cytokines were higher expressed while 11 kinds of cytokines were lower expressed by iMSCs.

iMSC presented similar cytokine profiles as primary MSCs. These cytokines are mainly relate to adhesion and migration molecules (CD105, ICAM, MCP-1, SDF-1, etc.), growth factors (GM-CSF, FGF, PDGF-AA, BDNF and HGF, etc.), immune cytokines (IL-6, IL-8, GRO-a, RANTES and IL17A, etc.), angiogenesis cytokines (VEGF, angiopoietin-2, Angiogenin and Chitinase 3-like 1) and osteogenesis cytokines (Osteopontin), which has been reported to be secreted by bone marrow MSCs before. It was also observed that the secretion profile was not exactly the same as the cell lysates profile, which indicated the potential of MSCs/iMSCs functions would be various depending on the stimulation and microenvironments. Therefore, it is necessary to examine the bioactivity of iMSCs on their immune-modulation effects.

HGF mediates mesenchymal stem cell-induced recovery in many diseases, such as multiple sclerosis in EAE mice [11] and ischemia/reperfusion-induced acute lung injury in rats [40]. HGF and its primary receptor cMet are critical in MSC-stimulated recovery in EAE, neural cell development and remyelination [11]. Active MSC-CM contained HGF, and exogenously supplied HGF promoted recovery in EAE. Therefore, the HGF level was further detected in the iMSC-CM and primary MCS-CM by human ELISA kit. It is found that about 10 pg/ml HGF was contained in iMSC-CM or MSC-CM (every 0.2×10^6 cells in 2 ml culture medium). Furthermore, it is aimed aimed to investigate the functional potential of these CMs in an available animal model, for example, EAE mouse model.

CD44 is a multifunctional cell surface molecule involved in cell adhesion, proliferation, differentiation, migration, angiogenesis, presentation of cytokines, chemokines and growth factors. It is also found that CD44 neutralizing antibodies (Hermes-1 or IM7) can impact on reduction of HGF by both iMSCs and MSCs after 18 hours treatments. However, this effect was mild when two different neutralizing antibodies used together. It was observed that the cells adherent ability was lost if the neutralizing process cost more than 48 hours (data not shown). Therefore, the CD44 is an essential factor for MSC survival and proteins secretion.

Example 4. Treatments with iMSCs and MSCs Conditional Medium can Improve Experimental Autoimmune Encephalomyelitis (EAE) Mice Recovery In order to investigate the immune modulating effect of iMSC, the culture supernatant was collected from iMSC and concentrated by centrifugation with filter devices. It is found that both iMSC-CM and MSC-CM can improve EAE mice recovery (FIG. 5) within 30 days. However, the equal amount of concentrated basal MSCs medium (DMEM-LG+ 10% FBS) caused mice severely pathogenic symptoms and death in 24 hours (n=4), which had to be euthanized according to the animal ethics. Therefore, it was not shown in statistically analysis figures.

This issue was also considered for the conditioned medium collected from iMSCs and MSCs. Therefore, a simple component size examination was performed by using NanoSight NS300 (Malvern Panalytical, UK) (FIGS. 9 and 10). Since DMEM-LG with 10% FBS was used for iMSC and MSC culturing, there was a large amount of component with the size between 50-100 nm. It is believed there were many from the FBS serum. But according to the EAE mouse experiments, after injection of concentrated and filtered DMEM-LG with 10% FBS medium, the mice were all dead. Thus, the exosome involved in the FBS was not useful for EAE treatment at least. For PBS injection group, the result of PBS solution had a peak with a larger size which might be the undissolved crystal or other disposes. For the comparison of iMSCs and MSCs, the size of CMs are mostly similar but with some minor difference. iMSCs-CM after 500 times dilution had 3 major peaks at 93 nm, 199 nm and 281 nm. While MSCs-CM after 100 times dilution had 3 major peaks at 103 nm. 226 nm and 299 nm. According to this data, it is believed that iMSC-CM had a higher enriched extracellular vehicles (EVs) compared to primary MSCs. Due to our experimental results, this CMs benefit for this EAE treatment but it also required further investigation and deeply understanding on how this EVs to work on immunomodulation and how to control the secretion profiles ex vivo.

Material and Methods

Reprogram Bone Marrow-Derived MSCs (BM-MSCs)

Figure 1:
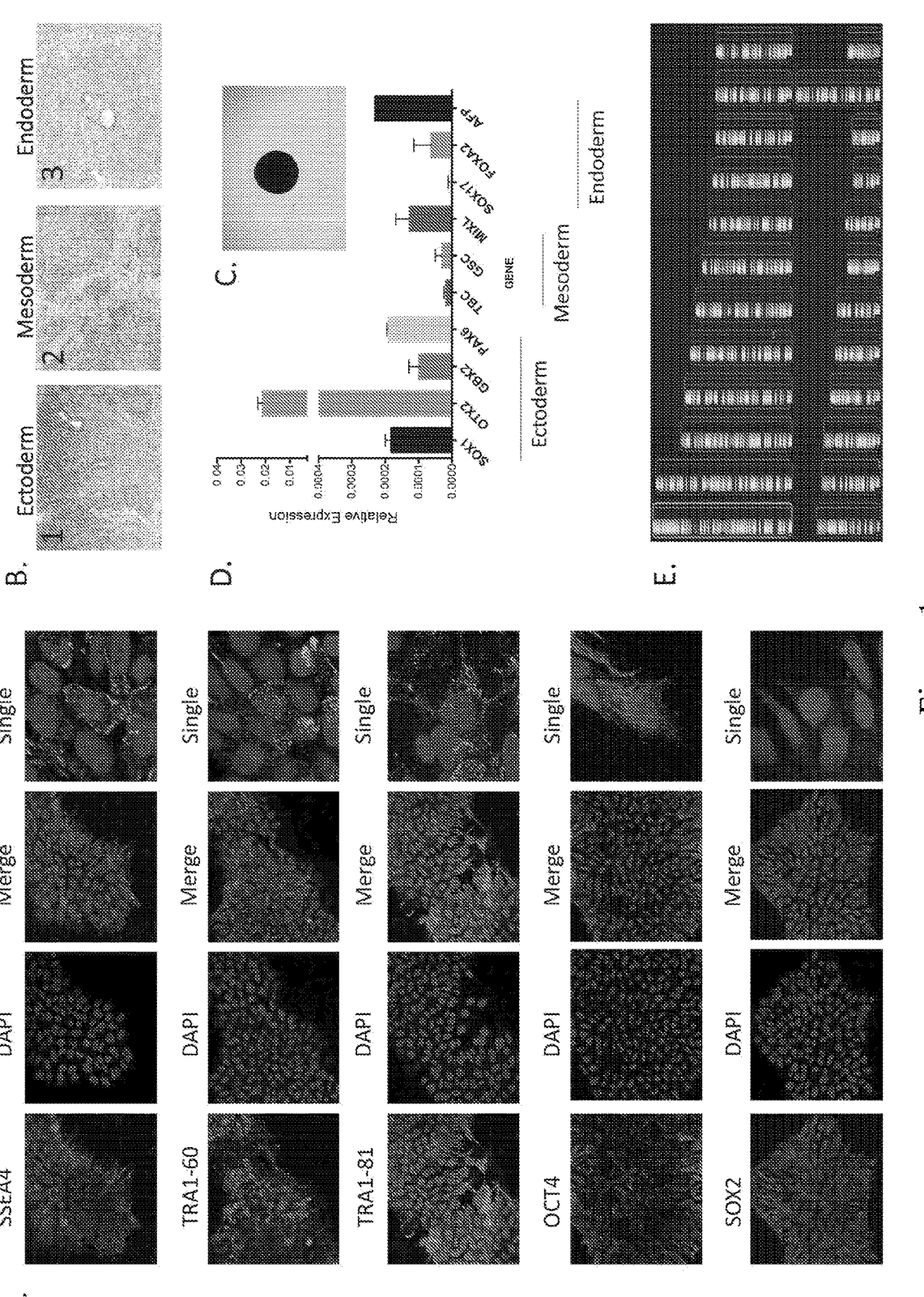
FIG. 1. Characterization of pluripotency of iPSCs derived from human MSCs. (A) Immunostaining with fluorescent antibodies of iPSCs specific markers of SEEA4, TRA-1-60 and TRA-1-81 as well as transcriptional factor SOX2 and with DAPI. (B) Xenografts of human iPSC cells generate well-differentiated teratoma-like masses containing three embryonic germ layers. Immunodeficient mouse recipients were injected with human iPSCs intramuscularly. Resulting teratomas demonstrated the following features in ectoderm B(1): neural rosettes, mesoderm B(2): muscle, and endoderm B(3): respiratory epithelium. (C) and (D): in vitro formation of embryoid body at day 7 in vitro. qPCR analyzed the relative expression levels of different respective genes of the three germ layers: Ectoderm (SOX1, OTX2, GBX2, PAX6); Mesoderm (TBC, GSC, MIXL); and Endoderm (SOX17, FOXA2, AFP). (E) Karyoview of iPSC_MD analyzed by SNP array.

Human primary bone marrow derived MSCs were cultured in DMEM-LG medium with 10% FBS within 8 passages. CytoTune™-iPS 2.0 Sendai Reprogramming Kit (A16517, Thermo Fisher Scientific, USA) was used and the reprogramming fibroblasts (Feeder-Free) protocol from the product's user guide was modified for BM-MSCs. Multiplicities of infection (MOI) used were KOS MOI=2.5-10, hc-Myc MOI=2.5-10, hKlf4 MOI=1.5-6. The best MOI was KOS MOI=8.75, hc-Myc MOI=8.75, hKlf4 MOI=4.5 (FIG. 1). For each sample, 1×10^5 cells were seeded in a well of a 6-well plate and reprogrammed. The BM-MSCs are seeded in DMEM-LG+10% FBS medium on day −2 and transduced cells are plated on Geltrex (Thermo, USA) coated plates on day 7. Gradient medium change was required for early reprogramming process. The best condition was Gradient 2 method: On day 9 change: 70% of (DMEM-LG with 10% FBS)+30% of E8 medium; on day 10 change: 30% of (DMEM-LG with 10% FBS)+70% of E8 medium; and on day 11 change: 100% of E8 medium (shown FIGS. 11 and 12). Reprogramming process was repeated with cells from four health donors independently (MD1, MD2, MD3 and MD4).

Comparison:

1.75× virus concentration+Gradient 2 medium replacing: (>20 colonies)

Normal virus concentration+Gradient 2 medium replacing: (3 colonies)

Normal virus concentration Gradient 1 medium replacing: 1 colony 1.75× virus concentration+Gradient 1 medium replacing: 2 colonies Immunofluorescence Staining For immunofluorescence staining, cells will be placed on the coverslip (12 mm for 24-well Deckglaser, 20643, Germany) coated with Geltrex (Thermo) cultured in 24-well and fixed with 4% PFA. Cells will be washed with rinse buffer (PBS with 0.2% BSA and 0.3% TritonX-100) for 2 min and incubated with blocking buffer (PBS with 5% BSA and 0.3% TritonX-100) for 2 h. After blocking, cells will be incubated with primary antibodies at 4° C. overnight. Mouse anti-human SSEA4 (MC-813-70, DSHB), mouse anti-human TRA-1-60 (41000, Invitrogen) and mouse anti-human TRA-1-81 (411100, Invitrogen); and rabbit anti-human Oct3/4 (A16555, Life Technologies) and rabbit anti-human SOX2 (481400, Invitrogen) were used. On the second day, the cells will be washed with rinse buffer for 3 times (15 min per time). Then incubate the secondary antibodies (Goat anti-mouse IgG Alexa 488, 1:800; Goat anti-rabbit IgG Alexa 647, 1:200; Thermo Fisher Scientific, US) for 2 h at room temperature. Afterwards, cells will also be incubated with DAPI (Cell Signaling Technology, US) for 5 min and rinsed for 3 times (5 min per time).

Teratoma Formation in SCID Mice

In order to evaluate and monitor the pluripotency of iPSCs, teratoma formation assay was applied on Prepared resuspending iPSC-MD cells in DPBS with 2× ROCK inhibitor Y-27632 (SCM075, Sigma-Aldrich) at a concentration of 1×10^6 cells per 50 μL of DPBS. And added an equal volume of chilled and liquid Matrigel (354248, Corning) together. Then gently mixed by using 25-gauge sterilized syringe and kept on ice until subcutaneous injection. The final injection volume of each mouse should be approximately 100 μL.

Quantitative Real-Time PCR (qPCR) of EBs

The expressions of pro-inflammatory factors were detected including SOX1, OTX2, GBX2, PAX6, TBC GSC, MIXL, SOX17, FOXA2 and AFP in the EBs by using qPCR method. In brief, EBs at day 7 were collected from the induction according to E6 medium protocol (Thermo). Total RNA was extracted Trizol Reagents (Invitrogen, USA) following the manufacturer's instructions. RNA quantification and purity were analyzed with Nanodrop (Thermo). The complementary DNA was synthesized by reverse transcript using Reverse Aid First Strand cDNA synthesis kit (Thermo Fisher Scientific, Rockford, IL, USA), Quantitative PCR was performed using the Maxima SYBR Green qPCR Master Mix (Thermo Fisher Scientific) and detected by StepOnePlus Real Time PCR (Thermo). The relative quantification of gene expression was conducted by $2^{-\Delta\Delta Ct}$ methods. Results were represented as relative fold changes normalized to an in-ternal control gene GAPDH.

Chromosomal Microarray (CMA) Analysis

Karyotyping analysis of iPSC_MD clone 19 and clone 16 were carried out by using chromosomal microarray (CMA) analysis as previous reported [41]. Genomic DNA (250 ng) which extracted from each sample was subjected to genome-wide copy number variation (CNV) and absence of heterozygosity (AOH) analyses using CytoScan 750 k SNP array (Affymetrix, Thermo Fisher Scientific). DNA was subjected to a series of restriction enzyme digestion, ligation, amplification, fragmentation, and labelling before loading onto the array for hybridization at 56° C. in GeneChip Hybridization Oven 645 (Affymetrix) according to manufacturer's instruction. After 18 hours of hybridization, the array will be washed in GeneChip Fluidics Station 450 (Affymetrix) before being scanned by GeneChip Scanner 3000 7G (Affymetrix). Results were visualized using Chromosome Analysis Suite (ChAS) version 4.0 (Affymetrix) and independently examined by two trained clinical scientists.

Generation of iMSC from Human ESCs or iPSCs

For differentiation of human ESCs/iPSCs into iMSCs, 7×10^4 cells were seeded on a well of 6-well plate coated with Geltrex (Thermo) containing DMEM/F12 (11320082, Thermo) with 10% FBS. Two methods were described as below and figures were shown in FIG. 11.

Method 1: (1) 20% knockout serum and 10 μM SB431542 (ab120163, Abcam) for 6 days. (2) Then replaced medium with DMEM/F12 with 10% knockout serum and 1 μM SB431542 for another 6 days. (3) Then cells were trypsinized for 5 minutes at 37° C. and 1×10^6 cells were seeded on a Geltrex coated or non-coated tissue culture 10 cm dish containing 8 ml of DMEM/F12 with 10% knockout serum and 10 ng/ml bFGF (13256029, Thermo) and 10 ng/ml EGF (PHG0311, Thermo) for 10 days. (4) Then medium was changed into DMEM-LG with 10% FBS in the following days. Medium were all changed every two days.

Method 2: (1) 10% knockout serum and 10 μM SB431542 (ab120163, Abcam) for 6 days. (2) Then replaced medium with DMEM/F12 with 1% BSA and 1× Insulin-Transferrin-Selenium (ITS-G) solution with 1 μM SB431542 for another 6 days. (3) Then cells were trypsinized for 5 minutes at 37° C. and 1×10^6 cells were seeded on a Geltrex coated or non-coated tissue culture 10 cm dish containing 8 ml of DMEM/F12 with 10% knockout serum and 10 ng/ml bFGF (13256029, Thermo) and 10 ng/ml EGF (PHG0311, Thermo) for 10 days. (4) Then medium was changed into DMEM-LG with 10% FBS in the following days. Medium were all changed every two days.

Method 1 and Method 2 were equally efficient, but the reagent cost in Method 2 was cheaper.

MSC Surface Marker Characterization by Flow Cytometry

Cells were harvested by trypsinization and washed with 2% FBS-PBS twice; 2×10^5 cells were re-suspended in 100 μl 2% FBS-PBS and incubated with the conjugated antibody for 30 min at room temperature in the dark. Stained cells were then washed with 2% FBS-PBS twice and re-suspended in 350 μl PBS for flow cytometry analysis (LSRII, BD); 10,000 events were recorded for each sample and data were analyzed with Flowjo. Antibodies against the human antigens CD11b conjugated Pacific Blue, CD19 conjugated APC, CD45 conjugated PerCPCy5.5, CD44 conjugated FITC, CD14 conjugated Pacific Blue, CD34 conjugated FITC, CD90 conjugated PerCPCy5.5, CD73 conjugated APC, CD105 conjugated PE and HLA-DR conjugated APC (BD, USA).

Transcriptome Analysis

Total RNAs were extracted using Trizol reagent according to the manufacturer's instructions. Transcriptome analysis by RNA-seq was performed at Novogene (HK) Co., Ltd. Briefly, mRNAs were enriched using poly-T oligo-attached magnetic beads, fragmented, and reverse transcribed into cDNAs. Sequencing libraries were prepared with the cDNAs and 150 bp pair-end reads were generated using an Illumina platform. Clean reads were mapped to reference genome using Tophat v2.0.12 with mismatch=2. HTSeq v0.6.1 was used to count the reads numbers mapped to each gene. Hierarchical clustering was performed using the log 10(FPKM+1) value. Differential expression analysis was performed with DEGSeq. Corrected P-value of 0.005 and log 2(Fold change) of 1 were set as the threshold for significantly differential expression.

The Proteome Profile of iMSCs and Human Primary MSCs

Human XL Cytokin Array was used to detect relative expression levels of individual analytes (ARY022, R&D Systems). $2\times10^5$ cells of iMSC-iPSC-MD1 and human primary MSCs MD1 were seeded on a well of 6-wells-plate in DMEM-LG supplemented with 2% FBS. Triplicate wells of each type of cells. For cell culture supernates, medium was collected after 48 hours and combined depending on cell types. For cell lysates, rinse cells with PBS and process the procedures following the manufacture protocol. For data analysis, the average signal (pixel density) of the pair of duplicate spots represented each analyte. Subtracted an averaged background signal from each spot. Used a negative control spots as a background value. Then compared corresponding signals on different arrays to determine the relative change in analyte levels between samples.

Active EAE Induction and iMSC/MSC Conditioned Medium Treatment

Female C57BL/6 N mice were immunized for active induction of EAE as our previous described [42]. Briefly, the mice were subcutaneously injected with 200 μg $MOG_{33-55}$ in complete Freund's adjuvant (5 mg/ml, Sigma-Aldrich). Pertussis Toxin (200 ng, List Biological Laboratories) was injected intravenously twice on 0- and 2-days post-immunization (dpi.). The immunized mice were daily monitored with body weight measurement and clinical score evaluation. EAE symptoms were scored for clinical severity as follows: 0, no clinical signs; 0.5, partially limp tail; 1, paralyzed tail; 1.5, hindlimb paresis or loss in coordinated movement; 2, loss in coordinated movement and hindlimb paresis; 2.5, one hindlimb paralyzed; 3, both hindlimbs paralyzed; 4, hindlimbs paralyzed, weakness in forelimbs; 5, forelimbs paralyzed [43, 44].

Human primary MD1 and MD2 and iMSCs-iPSC-MD1 and iMSCs-iPSC-MD2 were all grown in DMEM-LG supplemented with 10% FBS for 10 days. The growth medium was collected and refreshed every two days. Combined growth medium of MD1 and MD2 while combined growth medium of and iMSCs-iPSC-MD1 and iMSCs-iPSC-MD2, which to ensure that the results were not donor specific. Blank conditioned medium was DMEM-LG with 10% FBS alone. All conditioned medium was concentrated 100-fold through 30K and 100K centrifugal filter devices (Amicon Ultra-15). 15 ml of either iMSC-CM or MSC-CM from three independent repeats were combined and concentrated with centrifugal filter devices with an Amicon Ultra-15 (30K and 100K). Previous report has proved that hepatocyte growth factor (HGF) mediates MSCs stimulated functional recovery in animal models of MS [11]. Therefore, HGF in each concentrated fraction of iMSC-CM and MSC-CM was detected and quantified before intravenous injections (Table 1). In particular, HGF-enriched iMSCs-CM and MSCs-CM (>100 k) were prepared by using centrifugal filter devices (30K and 100K) and quantified by hHGF ELISA kit (n=4).

TABLE 1

The concentration of HGF/total protein in the concentrated medium

| | >100K | | 30K < X < 100K | | <30K | |
|---|---|---|---|---|---|---|
| | Total Protein (ug/ml) | HGF (pg/ml) | Total Protein (ug/ml) | HGF (pg/ml) | Total Protein (ug/ml) | HGF (pg/ml) |
| PBS | 0.00 | 0.00 | N.A. | N.A. | N.A. | N.A. |
| MSCs-CM | 1985.36 | 236 | 840.11 | 1.27 | 560.93 | 0.23 |
| iMSCs-CM | 1471.43 | 729 | 1055.84 | 5.11 | 554.59 | 0.00 |
| DMEM-LG + 10% FBS | 1875.11 | 0.00 | N.A. | N.A. | N.A. | N.A. |

Protein concentrations were estimated using the BCA Protein Assay Kit (23227, Thermo) and 3 mg/protein was used for in vivo treatments intravenously on day 18 at peak disease every other day for a total of three injections. Four groups of model mice had been included in, which were blank conditioned medium (n=3), PBS (n=5), iMSCs-CM (n=4) and MSCs-CM (n=4).

Histopathology

For H&E or Luxol fast blue (LFB) staining, mice (30 dpi) were perfused with PBS and then fixed with 4% paraformaldehyde (PFA). Isolated L4-L6 spinal cords were post fixed in 4% PFA overnight at 4° C., dehydrated in gradient ethanol, permeabilized with xylene, embedded into paraffin and cut into 5 μm sections. Slides were stained with H&E or LFB for assessment of inflammation and demyelination, respectively Inflammation and demyelination were scored as described previously [44]. Briefly, inflammation was scored as follows: 0, none; 1, a few inflammatory cells; 2, organization of perivascular infiltrates; and 3, increasing severity of perivascular cuffing with extension into the adjacent tissue; Demyelination was scored as follows: 0, none; 1, rare foci; 2, a few areas of demyelination; and 3, large (confluent) areas of demyelination.

Statistical Analysis

For comparison among multiple groups with one factor, statistical comparisons were made by one-way analysis of variance (ANOVA) following with multiple comparisons by using GraphPad Prism 6 (GraphPad software Inc, CA, USA). Each experiment was repeated for at least three times (n≥3). A P value of <0.05 was considered as statistically significant. Three different symbols were denoted as: *P<0.05, P<0.01, and *P<0.001. All values were expressed as mean±SEM.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference herein in their entireties.

REFERENCE

1. Hu, S., et al., *Effects of cellular origin on differentiation of human induced pluripotent stem cell-derived endothelial cells.* JCI Insight, 2016. 1(8).

2. Kyttala, A., et al., *Genetic Variability Overrides the Impact of Parental Cell Type and Determines iPSC Differentiation Potential*. Stem Cell Reports, 2016. 6(2): p. 200-12.

3. Sell, S., ed. *Stem Cells Handbook*. 2013, Springer Science & Business Media.

4. Becker, A. J., C. E. Mc, and J. E. Till, *Cytological demonstration of the clonal nature of spleen colonies derived from transplanted mouse marrow cells*. Nature, 1963. 197: p. 452-4.

5. Friedenstein, A. J., R. K. Chailakhjan, and K. S. Lalykina, *The development of fibroblast colonies in monolayer cultures of guinea-pig bone marrow and spleen cells*. Cell Tissue Kinet, 1970. 3(4): p. 393-403.

6. Dominici, M., et al., *Minimal criteria for defining multipotent mesenchymal stromal cells. The International Society for Cellular Therapy position statement*. Cytotherapy, 2006. 8(4): p. 315-7.

7. Deng, R., Law, A. H. Y., Shen, J., Chan, G. C., *Mini Review: Application of Human Mesenchymal Stem Cells in Gene and Stem Cells Therapy Era*. Current Stem Cell Reports, 2018. 4(4): p. 10.

8. Ankrum, J. A., J. F. Ong, and J. M. Karp, *Mesenchymal stem cells: immune evasive, not immune privileged*. Nat Biotechnol, 2014. 32(3): p. 252-60.

9. Kyurkchiev, D., et al., *Secretion of immunoregulatory cytokines by mesenchymal stem cells*. World J Stem Cells, 2014. 6(5): p. 552-70.

10. Galipeau, J. and L. Sensebe, *Mesenchymal Stromal Cells: Clinical Challenges and Therapeutic Opportunities*. Cell Stem Cell, 2018. 22(6): p. 824-833.

11. Bal, L., et al., *Hepatocyte growth factor mediates mesenchymal stem cell-induced recovery in multiple sclerosis models*. Nat Neurosci, 2012. 15(6): p. 862-70.

12. Kato, A., et al., *Assignment of the human alpha 2-plasmin inhibitor gene (PLI) to chromosome region 18p11.1 - - - q11.2 by in situ hybridization*. Cytogenet Cell Genet, 1988. 47(4): p. 209-11.

13. Mihara, K., et al., *Development and functional characterization of human bone marrow mesenchymal cells immortalized by enforced expression of telomerase*. Br J Haematol, 2003. 120(5): p. 846-9.

14. Lian, Q., et al., *Functional mesenchymal stem cells derived from human induced pluripotent stem cells attenuate limb ischemia in mice*. Circulation, 2010. 121 (9): p. 1113-23.

15. Takahashi, K., et al., *Induction of pluripotent stem cells from adult human fibroblasts by defined factors*. Cell, 2007. 131(5): p. 861-72.

16. Takahashi, K. and S. Yamanaka, *Induction of pluripotent stem cells from mouse embryonic and adult fibroblast cultures by defined factors*. Cell, 2006. 126(4): p. 663-76.

17. Malik, N. and M. S. Rao, *A review of the methods for human iPSC derivation*. Methods Mol Biol, 2013. 997: p. 23-33.

18. Warren, L., et al., *Highly efficient reprogramming to pluripotency and directed differentiation of human cells with synthetic modified mRNA*. Cell Stem Cell, 2010. 7(5): p. 618-30.

19. Subramanyam, D., et al., *Multiple targets of miR-302 and miR-372 promote reprogramming of human fibroblasts to induced pluripotent stem cells*. Nat Biotechnol, 2011. 29(5): p. 443-8.

20. Anokye-Danso, F., et al., *Highly efficient miRNA-mediated reprogramming of mouse and human somatic cells to pluripotency*. Cell Stem Cell, 2011. 8(4): p. 376-88.

21. Miyoshi, N., et al., *Reprogramming of mouse and human cells to pluripotency using mature microRNAs*. Cell Stem Cell, 2011. 8(6): p. 633-8.

22. Kaji, K., et al., *Virus free induction of pluripotency and subsequent excision of reprogramming factors*. Nature, 2009. 458(7239): p. 771-5.

23. Narsinh, K. H., et al., *Generation of adult human induced pluripotent stem cells using nonviral minicircle DNA vectors*. Nat Protoc, 2011. 6(1): p. 78-88.

24. Okita, K., et al., *Generation of mouse induced pluripotent stem cells without viral vectors*. Science, 2008. 322 (5903): p. 949-53.

25. Loh, Y. H., et al., *Reprogramming of T cells from human peripheral blood*. Cell Stem Cell, 2010. 7(1): p. 15-9.

26. Staerk, J., et al., *Reprogramming of human peripheral blood cells to induced pluripotent stem cells*. Cell Stem Cell, 2010. 7(1): p. 20-4.

27. Wiley, L. A., et al., *Generation of Xeno-Free, cGMP-Compliant Patient-Specific iPSCs from Skin Biopsy*. Curr Protoc Stem Cell Biol, 2017. 42: p. 4A 12 1-4A 12 14.

28. Megges, M., et al., *Generation of an iPS cell line from bone marrow derived mesenchymal stromal cells from an elderly patient*. Stem Cell Res, 2015. 15(3): p. 565-8.

29. Re, S., et al., *Improved Generation of Induced Pluripotent Stem Cells From Hair Derived Keratinocytes—A Tool to Study Neurodevelopmental Disorders as ADHD*. Front Cell Neurosci, 2018. 12: p. 321.

30. Boonkaew, B., et al., *Establishment of an integration free induced pluripotent stem cell line (MUSIi005-A) from exfoliated renal epithelial cells*. Stem Cell Res, 2018. 30: p. 34-37.

31. Zhang, S. Z., et al., *Urine-derived induced pluripotent stem cells as a modeling tool for paroxysmal kinesigenic dyskinesia*. Biol Open, 2015. 4(12): p. 1744-52.

32. Zhou, T., et al., *Generation of human induced pluripotent stem cells from urine samples*. Nat Protoc, 2012. 7(12): p. 2080-9.

33. Bilousova, G., et al., *Osteoblasts derived from induced pluripotent stem cells form calcified structures in scaffolds both in vitro and in vivo*. Stem Cells, 2011. 29(2): p. 206-16.

34. Villa-Diaz, L. G., et al., *Derivation of mesenchymal stem cells from human induced pluripotent stem cells cultured on synthetic substrates*. Stem Cells, 2012. 30(6): p. 1174-81.

35. Kagia, A., et al., *Therapeutic Effects of Mesenchymal Stem Cells Derived From Bone Marrow, Umbilical Cord Blood, and Pluripotent Stem Cells in a Mouse Model of Chemically Induced Inflammatory Bowel Disease*. Inflammation, 2019. 42(5): p. 1730-1740.

36. Khan, M. A., et al., *iPSC-derived MSC therapy induces immune tolerance and supports long-term graft survival in mouse orthotopic tracheal transplants*. Stem Cell Res Ther, 2019. 10(1): p. 290.

37. Yang, H., et al., *Human induced pluripotent stem cell-derived mesenchymal stem cells promote healing via TNF-alpha-stimulated gene-6 in inflammatory bowel disease models*. Cell Death Dis, 2019. 10(10): p. 718.

38. Cuascut, F. X. and G. J. Hutton, *Stem Cell-Based Therapies for Multiple Sclerosis: Current Perspectives*. Biomedicines, 2019. 7(2).

39. Guilak, F., et al., *Designer Stem Cells: Genome Engineering and the Next Generation of Cell-Based Therapies*. J Orthop Res, 2019. 37(6): p. 1287-1293.

40. Chen, S., et al., *Hepatocyte growth factor-modified mesenchymal stem cells improve ischemia/reperfusion-induced acute lung injury in rats*. Gene Ther, 2017. 24(1): p. 3-11.

41. D'Antonio, M., et al., *High-Throughput and Cost-Effective Characterization of Induced Pluripotent Stem Cells*. Stem Cell Reports, 2017. 8(4): p. 1101-1111.

42. Li, W., et al., *Radix Rehmanniae Extract Ameliorates Experimental Autoimmune Encephalomyelitis by Suppressing Macrophage-Derived Nitrative Damage*. Front Physiol, 2018. 9: p. 864.

43. Stromnes, I. M. and J. M. Goverman, *Active induction of experimental allergic encephalomyelitis*. Nat Protoc, 2006. 1(4): p. 1810-9.

44. Wu, H., et al., *Caveolin-1 Is Critical for Lymphocyte Trafficking into Central Nervous System during Experimental Autoimmune Encephalomyelitis*. J Neurosci, 2016. 36(19): p. 5193-9.

45. Ksiazek, K., *A comprehensive review on mesenchymal stem cell growth and senescence*. Rejuvenation Res, 2009. 12(2): p. 105-16.

46. Trento, C. and F. Dazzi, *Mesenchymal stem cells and innate tolerance: biology and clinical applications*. Swiss Med Wkly, 2010. 140: p. w13121.

47. Ng, F., et al., *PDGF, TGF-beta, and FGF signaling is important for differentiation and growth of mesenchymal stem cells (MSCs): transcriptional profiling can identify markers and signaling pathways important in differentiation of MSCs into adipogenic, chondrogenic, and osteogenic lineages*. Blood, 2008. 112(2): p. 295-307.

48. Sackstein, R., et al., *Ex vivo glycan engineering of CD44 programs human multipotent mesenchymal stromal cell trafficking to bone*. Nat Med, 2008. 14(2): p. 181-7.

We claim:

1. A method for generating induced mesenchymal stromal cells (iMSCs) comprising:

obtaining induced pluripotent stem cells (iPSCs) from reprogrammed human fibroblasts (iPSC_Fb) and human primary mesenchymal stromal cells (MSCs);

culturing the iPSCs with a first medium for about 6 days;

replacing the first medium with a second medium and culturing the cells with the second medium for about 6 days;

trypsinizing the cultured cells;

seeding the trypsinized cells on a coated or non-coated tissue culture with a third medium for about 10 days; and replacing the third medium with a fourth medium and culturing the seeded cells for 10 days, wherein the human primary MSCs are bone marrow derived (BM MSCs), wherein a reprogramming of MSCs comprises nonintegrating Sendai virus vector transduction with the addition of Yamanaka transcriptional factors, wherein the first medium comprises:

a Dulbecco's Modified Eagle Medium: Nutrient Mixture F-12 (DMEM/F12);

a knockout serum; and a transforming growth factor (TGF) beta and anaplastic lymphoma kinase (ALK) inhibitor, wherein the second medium comprises:

DMEM/F12;

a TGF beta and ALK inhibitor; and a knockout serum or an Insulin-Transferrin-Selenium (ITS-G) solution, wherein the third medium comprises:

DMEM/F12;

a knockout serum; and a basic fibroblast growth factor (bFGF) and an epidermal growth factor (EGF)

wherein the fourth medium comprises:

Dulbeccos' Modified Eagle medium-Low Glucose (DMEM-LG) medium and is optionally supplemented with fetal bovine serum (FBS), wherein media were changed every two days.

* * * * *